United States Patent
Choi

(10) Patent No.: US 9,162,975 B2
(45) Date of Patent: Oct. 20, 2015

(54) PHENYL CARBAMATE COMPOUNDS FOR USE IN ALLEVIATING OR TREATING PAIN

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd. (KR)

( * ) Notice: Subject to any disclaimer, the term of this patent is extended or adjusted under 35 U.S.C. 154(b) by 2 days.

(21) Appl. No.: 13/727,663

(22) Filed: Dec. 27, 2012

(65) Prior Publication Data

US 2013/0165409 A1 Jun. 27, 2013

Related U.S. Application Data

(60) Provisional application No. 61/580,409, filed on Dec. 27, 2011.

(51) Int. Cl.
| | |
|---|---|
| C07C 271/02 | (2006.01) |
| A61K 31/165 | (2006.01) |
| A61K 31/047 | (2006.01) |
| A61K 31/164 | (2006.01) |
| C07C 33/26 | (2006.01) |
| C07C 271/12 | (2006.01) |
| C07C 271/24 | (2006.01) |
| C07F 7/18 | (2006.01) |
| C07C 271/28 | (2006.01) |
| C07C 271/16 | (2006.01) |
| A61K 31/325 | (2006.01) |

(52) U.S. Cl.
CPC ............. *C07C 271/02* (2013.01); *A61K 31/047* (2013.01); *A61K 31/164* (2013.01); *A61K 31/165* (2013.01); *A61K 31/325* (2013.01); *C07C 33/26* (2013.01); *C07C 271/12* (2013.01); *C07C 271/16* (2013.01); *C07C 271/24* (2013.01); *C07C 271/28* (2013.01); *C07F 7/1804* (2013.01); *C07C 2101/02* (2013.01); *C07C 2101/14* (2013.01); *C07C 2102/42* (2013.01)

(58) Field of Classification Search
CPC .... A61K 31/15; A61K 31/325; C07C 271/02; C07C 271/12; C07C 271/16; C07F 7/1804
USPC ............................................ 514/476, 63, 730
See application file for complete search history.

(56) References Cited

U.S. PATENT DOCUMENTS

| | | | |
|---|---|---|---|
| 2,884,444 A | 4/1959 | Berger et al. | |
| 2,937,119 A | 5/1960 | Berger et al. | |
| 3,265,727 A | 8/1966 | Bossinger et al. | |
| 3,265,728 A * | 8/1966 | Bossinger et al. | 560/164 |
| 3,313,692 A | 4/1967 | Bossinger et al. | |
| 3,313,696 A * | 4/1967 | Bossinger et al. | 514/489 |
| 3,313,699 A | 4/1967 | Bossinger et al. | |
| 3,313,700 A | 4/1967 | Bossinger et al. | |
| 3,600,427 A | 8/1971 | Verbiscar | |
| 6,103,759 A | 8/2000 | Choi et al. | |
| 7,385,076 B2 | 6/2008 | Patel et al. | |
| 7,442,438 B2 | 10/2008 | Boulos et al. | |
| 7,737,141 B2 | 6/2010 | Kimura et al. | |
| 2001/0034365 A1 | 10/2001 | Choi et al. | |
| 2002/0156127 A1* | 10/2002 | Plata-Salaman et al. | 514/483 |
| 2002/0165273 A1 | 11/2002 | Plata-salaman et al. | |
| 2004/0138299 A1 | 7/2004 | Cahill et al. | |
| 2006/0194873 A1 | 8/2006 | Choi et al. | |
| 2008/0090903 A1 | 4/2008 | Pandey et al. | |
| 2008/0103198 A1 | 5/2008 | Haas | |
| 2008/0317883 A1 | 12/2008 | Choi et al. | |
| 2009/0048213 A1 | 2/2009 | Kimura et al. | |
| 2009/0221640 A1 | 9/2009 | Briggner et al. | |
| 2012/0184762 A1 | 7/2012 | Choi | |
| 2013/0005801 A1 | 1/2013 | Choi | |
| 2013/0165408 A1 | 6/2013 | Choi et al. | |
| 2013/0165410 A1 | 6/2013 | Choi et al. | |
| 2013/0165509 A1 | 6/2013 | Choi et al. | |
| 2013/0184338 A1 | 7/2013 | Choi | |
| 2013/0203846 A1 | 8/2013 | Choi | |
| 2014/0051753 A9 | 2/2014 | Choi | |

FOREIGN PATENT DOCUMENTS

| | | |
|---|---|---|
| CN | 1208402 A | 2/1999 |
| CN | 1536992 A | 10/2004 |
| CN | 1536993 A | 10/2004 |
| CN | 101208402 A | 6/2008 |
| CN | 101472913 A | 7/2009 |

(Continued)

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*

Sheridan, R.P. "The Most Common Chemical Replacements in Drug-Like Compounds" J. Chem. Inf. Comupt. Sci., 2002, vol. 42, pp. 103-108.*

U.S. Appl. No. 13/727,654, Response filed Dec. 9, 2013 to Non Final Office Action mailed Sep. 9, 2013, 17 pgs.

(Continued)

*Primary Examiner* — Kendra D Carter
(74) *Attorney, Agent, or Firm* — Schwegman Lundberg & Woessner, P.A.

(57) ABSTRACT

A phenyl carbamate compound; a composition for treating and/or alleviating pain containing the phenyl carbamate compound or a pharmaceutically acceptable salt thereof as an active ingredient; a method of treating and/or alleviating pain comprising administering the phenyl carbamate compound or a pharmaceutically acceptable salt thereof to a patient in need of pain treatment; and a use of the phenyl carbamate compound or a pharmaceutically acceptable salt thereof in treating and/or alleviating pain, are provided.

8 Claims, 4 Drawing Sheets

(56) References Cited

FOREIGN PATENT DOCUMENTS

| JP | 61-271992 A | 12/1986 |
|---|---|---|
| WO | WO-2006/033947 A2 | 3/2006 |
| WO | WO-2008/013213 A1 | 1/2008 |
| WO | WO-2008/124848 A1 | 10/2008 |
| WO | WO 2012002773 A2 * | 5/2012 |
| WO | WO-2012/096458 A2 | 7/2012 |

OTHER PUBLICATIONS

U.S. Appl. No. 13/727,661, Response filed Nov. 15, 2013 to Restriction Requirement mailed Oct. 15, 2013, 6 pgs.
Lehmkuhle, M. J, et al., "A Simple Quantitative Method for Analyzing Electrographic Status Epilepticus in Rats", *J Neurophysiol.*, 101, (Mar. 2009), 1660-1670.
U.S. Appl. No. 13/727,654, Response filed Aug. 16, 2013 to Restriction Requirement mailed Jul. 31, 2013, 6 pgs.
U.S. Appl. No. 13/727,654, Restriction Requirement mailed Jul. 31, 2013, 7 pgs.
International Application Serial No. PCT/KR2012/011469, International Search Report mailed Apr. 22, 2013, 4 pgs.
International Application Serial No. PCT/KR2012/011469, Written Opinion mailed Apr. 22, 2013, 7 pgs.
International Application Serial No. PCT/KR2012/011470. International Search Report mailed Apr. 22, 2013, 4 pgs.
International Application Serial No. PCT/KR2012/011470. Written Opinion mailed Apr. 22, 2013, 5 pgs.
International Application Serial No. PCT/KR2012/011471, International Search Report mailed Apr. 22, 2013, 4 pgs.
International Application Serial No. PCT/KR2012/011471, Written Opinion mailed Apr. 22, 2013, 5 pgs.
International Application Serial No. PCT/KR2012/011472, International Search Report mailed Apr. 23, 2013, 4 pgs.
International Application Serial No. PCT/KR2012/011472, Written Opinion mailed Apr. 23, 2013, 5 pgs.
International Application Serial No. PCT/KR2012/011474, International Search Report mailed Apr. 23, 2013, 4 pgs.
International Application Serial No. PCT/KR2012/011474, Written Opinion mailed Apr. 23, 2013, 5 pgs.
International Application Serial No. PCT/KR2012/011475, International Search Report mailed Apr. 23, 2013, 4 pgs.
International Application Serial No. PCT/KR2012/011475, Written Opinion mailed Apr. 23, 2013, 5 pgs.
Girijavallabhan, V. M., "Synthesis of the Antifungal Agent Sch 42427 (SM 9164)", *Bioorganic & Medicinal Chemistry Letters*, 1(7), (1991), 349-352.
Jiao, P., et al., "A Sequential O-Nitrosoaldol and Grignard Addition Process: An Enantio- and Diastereoselective Entry to Chiral 1,2-Diols", *Angewandte Chemie, International Edition*, 48(18), (2009), 3333-3336.
U.S. Appl. No. 13/727,654, Non Final Office Action mailed Sep. 9, 2013, 21 pgs.
U.S. Appl. No. 13/727,661, Restriction Requirement mailed Oct. 15, 2013, 6 pgs.
"Epilepsy", bu Mayo Clinic Staff, [online]. Retrieved from the Internet: <URL: http://www.mayoclinic.com/health/epilepsy/DS00342/METHOD =print&DSECTION=all>, (2013), 14 pgs.
U.S. Appl. No. 13/727,654, Final Office Action mailed Jan. 29, 2014, 27 pgs.
U.S. Appl. No. 13/727,659, Non Final Office Action mailed Apr. 22, 2014, 6 pgs.
U.S. Appl. No. 13/175,025, Final Office Action mailed Sep. 26, 2014, 8 pgs.
U.S. Appl. No. 13/175,025, Final Office Action mailed Oct. 10, 2013, 10 pgs.
U.S. Appl. No. 13/175,025, Non Final Office Action mailed Mar. 20, 2014, 9 pgs.
U.S. Appl. No. 13/175,025, Non Final Office Action mailed May 16, 2013, 19 pgs.
U.S. Appl. No. 13/175,025, Response filed Jan. 10, 2014 to Final Office Action mailed Oct. 10, 2013, 25 pgs.
U.S. Appl. No. 13/175,025, Response filed Aug. 16, 2013 to Non Final Office Action mailed May 16, 2013, 28 pgs.
U.S. Appl. No. 13/175,025, Response filed Aug. 20, 2014 to Non Final Office Action mailed Mar. 20, 2014, 25 pgs.
U.S. Appl. No. 13/175,025, Supplemental Amendment filed Sep. 13, 2013, 7 pgs.
U.S. Appl. No. 13/338,863, Non Final Office Action mailed Dec. 10, 2013, 5 pgs.
U.S. Appl. No. 13/338,863, Notice of Allowance mailed Apr. 29, 2014, 9 pgs.
U.S. Appl. No. 13/338,863, Response filed Mar. 6, 2014 to Non Final Ofifce Action mailed Dec. 10, 2013, 10 pgs.
U.S. Appl. No. 13/338,863, Response filed Oct. 28, 2013 to Restriction Requirement mailed Sep. 27, 2013, 9 pgs.
U.S. Appl. No. 13/338,863, Restriction Requirement mailed Sep. 27, 2013, 9 pgs.
U.S. Appl. No. 13/727,654, Examiner Interview Summary mailed May 29, 2014, 3 pgs.
U.S. Appl. No. 13/727,654, Response filed Jun. 27, 2014 to Final Office Action mailed Jan. 29, 2014, 21 pgs.
U.S. Appl. No. 13/727,659, Notice of Allowance mailed Sep. 23, 2014, 7 pgs.
U.S. Appl. No. 13/727,659, Response filed Aug. 22, 2014 to Non Final Office Action mailed Apr. 22, 2014, 37 pgs.
U.S. Appl. No. 13/727,661, Non Final Office Action mailed Jun. 24, 2014, 10 pgs.
U.S. Appl. No. 13/727,661, Preliminary Amendment filed Mar. 28, 2013, 4 pgs.
U.S. Appl. No. 13/727,661, Response filed Sep. 19, 2014 to Non Final Office Action mailed Jun. 24, 2014, 9 pgs.
U.S. Appl. No. 13/727,665, Restriction Requirement mailed Sep. 5, 2014, 6 pgs.
Canadian Application Serial No. 2,815,460, Office Action mailed Mar. 6, 2014, 4 pgs.
Chinese Application Serial No. 201180032939.0, Office Action dated Mar. 31, 2014, (w/ English Translation), 8 pgs.
Chinese Application Serial No. 201180032939.0, Office Action dated Sep. 17, 2013, (w/ English Translation), 12 pgs.
Chinese Application Serial No. 201180063001.5, Office Action mailed Mar. 14, 2014, (w/ English Translation), 13 pgs.
European Application Serial No. 12169507.6, European Search Report maled Sep. 26, 2012, 8 pgs.
European Application Serial No. 12169507.6, Office Action mailed Feb. 21, 2014, 6 pgs.
International Application Serial No. PCT/KR2011/004862, International Search Report mailed Feb. 27, 2012, 3 pgs.
International Application Serial No. PCT/KR2011/004862, Written Opinion mailed Feb. 27, 2012, 5 pgs.
International Application Serial No. PCT/KR2011/010105, International Search Report mailed Aug. 7, 2012, 3 pgs.
International Application Serial No. PCT/KR2011/010105, Written Opinion mailed Aug. 7, 2012, 4 pgs.
Japanese Application Serial No. 2013-518264, Office Action mailed Mar. 11, 2014, (w/ English Translation), 6 pgs.
Amarante, G. W., et al., "Acyloins from Morita-Baylis-Hillman adducts: an alternative approach to the racemic total synthesis of bupropion", *Tettrahedron Letters*, 49, (2008), 3744-3748.
Bausch, C. C., et al., "Cross Silyl Benzoin Additions Catalyzed by Lanthanum Tricyanide", *J. Org. Chem.*, 69, (2004), 4283-4285.
Citterio, A., et al., "Electron-transfer Processes: Oxidation of a-and β-Alkenylbenzenes by Peroxydisulphate in Acetic Acid", *J. Chem. Soc. Perkin Tran. I*, (1983), 891-896.
Edin, Michaela, et al., "Ruthenium- and lipase-catalyzed DYKAT of 1,2-diols: an enantioselective synthesis of syn-1,2-diacetates", *Tetrahedron: Asymmetry*, 17(4), (2006), 708-715.
Eid, Jr., C. N., et al., "Enantiomerically Pure Ketals in Synthesis, Diastereoselective Formation of Beta-Keto and Beta-Hydroxy Ketals", *Tetrahedron Letters*, 32(4), (1991), 461-464.

(56) References Cited

OTHER PUBLICATIONS

Ghosh, Nayan, et al., "Gold-Catalyzed Regioselective Hydration of Propargyl Acetates Assisted by a Neighboring Carbonyl Group: Access to a-Acyloxy Methyl Ketones and Synthesis of (±)-Actinopolymorphol B", *J. Org. Chem.*, (2010), 500-511.

Girijavallabhan, V. M., et al., "Synthesis of the antifungal agent SCH 42427 (SM 9164)",(Abstract), *Bioorganic & Medicinal Chemistry Letters*, 1(7), 349-352, ASC on STN, Accession No. 1992:41371, (1991), 1 pg.

Joseph, S. P., et al., "Reaction of chlorosulfonyl isocyanate with 1,2-diols", *Synthetic Communications*, 18(18), (1988), 2295-2302.

Morimoto, Takashi, et al., "Oxidation by cobalt(III) acetate. Part 10. Effects of ring substituents on the product distributions in the oxidation of β-methylstyrenes by cobalt(III) acetate in acetic acid", *J. Chem. Soc. Perkin Trans. II*, (1986), 1205-1209.

Ohta, Hiromichi, et al., "Reductive C2-Homologation of Substituted Benzaldehydes by Fermenting Baker's Yeast", *Agric. Biol. Chem.*, 50(5), (1986), 1261-1266.

Wijesekera, L. C., et al., "Amyotrophic lateral sclerosis", *Orphanet Journal of Rare Diseases*, 4:3, (2009), 1-22.

* cited by examiner

Compound 65
(50mg/kg, po, Test at 1hr)

Compound 1
(ED50 : 3.4 mg/kg, ip, Test at 0.5hr)

PHENYL CARBAMATE COMPOUNDS FOR USE IN ALLEVIATING OR TREATING PAIN

CROSS-REFERENCE TO RELATED APPLICATION

This application claims priority to and the benefit of U.S. Provisional Application No. 61/580,409, filed in the United States Patent and Trademark Office on Dec. 27, 2011, the entire contents of which are incorporated herein by reference.

TECHNICAL FIELD

A phenyl carbamate compound; a composition for treating and/or alleviating pain containing the phenyl carbamate compound or a pharmaceutically acceptable salt thereof as an active ingredient; a method of treating and/or alleviating pain comprising administering the phenyl carbamate compound or a pharmaceutically acceptable salt thereof to a patient in need of pain treatment; and a use of the phenyl carbamate compound or a pharmaceutically acceptable salt thereof in treating and/or alleviating pain, are provided.

BACKGROUND ART

Pain is one of the most common reasons for a patient to seek medical care and in consequence, pain results in a tremendous number of lost work days per year.

Pain is an unpleasant feeling often caused by intense or damaging stimuli, such as stubbing a toe, burning a finger, putting alcohol on a cut, and bumping the funny bone. The International Association for the Study of Pain's widely used definition states: "Pain is an unpleasant sensory and emotional experience associated with actual or potential tissue damage, or described in terms of such damage". Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation. It is a major symptom in many medical conditions, and can significantly interfere with a persons quality of life and general functioning. Psychological factors such as social support, hypnotic suggestion, excitement, or distraction can significantly modulate pain's intensity or unpleasantness.

In 1994, responding to the need for a more useful system for describing chronic pain, the International Association for the Study of Pain (IASP) classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology.

This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system or by its abnormal function (dysfunctional pain, like in fibromyalgia, irritable bowel syndrome, tension type headache, etc.).

In nociceptive pain, the stimulation of the sensory nerve endings called nociceptors causes the sensation of pain. Such pain often occurs after injury or surgery. The pain signals are transmitted by the nociceptors to the brain. Often the pain is localised, constant and has an aching or throbbing quality. Once the damage to the tissue heals the pain usually resolves. Treatment with opioids may resolve nociceptive pain. Psychogenic pain is a pain disorder that is associated with psychological factors. Some types of mental or emotional problems can cause pain. They can also increase or prolong pain. Upper back pain, low back pain and stomach pains are some of the most common types of psychogenic pain. People with this pain disorder actually have real pain. The diagnosis is made when all physical causes of pain are ruled out.

Neuropathic pain is caused by abnormalities in the nerves, spinal cord or brain and is a chronic type of non-malignant pain with an estimated prevalence of over 1% of the population. Optimizing pain relief in these patients is crucial in helping a patient regain control of his or her life. The most common cause of neuropathic pain is injury or dysfunction of nerves. Injury or dysfunction of peripheral nerves or nerves descending from the spinal cord results in disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's.

Therefore, it is needed to develop therapeutic measures for treating or alleviating pain.

SUMMARY OF THE INVENTION

An embodiment provides an organic compound, i.e., phenyl carbamate compound. More particularly, the embodiment is directed to a phenyl carbamate compound of the following Chemical Formula 1; a racemate, an enantiomer, a diastereomer, a mixture of enantiomers, or a mixture of diastereomers thereof; or a pharmaceutically acceptable salt thereof. The compound has remarkably excellent treatment and/or alleviation effect on pain as well as very low toxicity. Therefore, the compounds of formula I may be useful as a drug for the treatment and/or alleviation of pain:

[Chemical Formula 1]

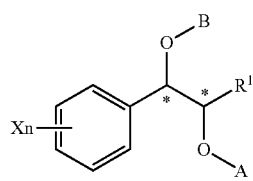

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

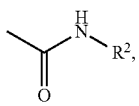

B is hydrogen, a carbamoyl derivative represented by

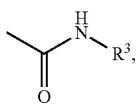

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not the carbamoyl derivative at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

Another embodiment provides a pharmaceutical composition for of alleviating and/or treating pain containing a compound of Chemical Formula 1; a racemate, an enantiomer, a diastereomer, a mixture of enantiomers, or a mixture of diastereomers thereof; or a pharmaceutically acceptable salt thereof, as an active ingredient Another embodiment provides a method of alleviating and/or treating pain comprising administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of alleviating and/or treating pain.

Another embodiment provides a use of a phenyl carbamate compound represented by Chemical Formula 1; a racemate, an enantiomer, a diastereomer, a mixture of enantiomers, or a mixture of diastereomers thereof; or a pharmaceutically acceptable salt thereof, in the alleviation and/or treatment of pain or in the manufacture of a pharmaceutical composition for alleviating and/or treating pain.

DETAILED DESCRIPTION OF THE EMBODIMENTS

Continuing its research work in the field of pain, the present inventors, as results of studies on the development of anti-pain drugs, found that a phenyl carbamate compounds of the following Chemical Formula 1 exhibits remarkably excellent anti-pain activity in various emulation models and simultaneously has very low toxicity, to complete the invention.

An embodiment provides an organic compound, particularly, a phenyl carbamate compound, more particularly, a phenyl carbamate compound represented by following Chemical Formula 1; a racemate, an enantiomer, a diastereomer, a mixture of enantiomers, or a mixture of diastereomers thereof; or a pharmaceutically acceptable salt thereof:

[Chemical Formula 1]

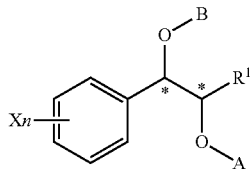

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

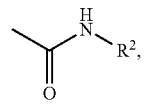

B is hydrogen, a carbamoyl derivative represented by

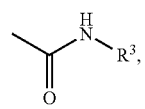

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not the carbamoyl derivative at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

In a concrete embodiment, the phenyl carbamate compound may be selected from the group consisting of:
1-(2-chlorophenyl)-1-hydroxypropyl-2-carbamate,
1-(2-chlorophenyl)-1-hydroxybutyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate,
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate.

In this compound, 2 chiral carbons exist at positions 1 and 2 from phenyl group substituted with X; thus, the compound may exist in the form of an enantiomer, a diastereomer, a mixture of enantiomers, or a mixture of diastereomers, as well as a racemate.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

As demonstrated in the following experimental examples, the compound of Chemical Formula 1, a racemate, an enantiomer, a diastereomer, a mixture of enantiomers, or a mixture of diastereomers thereof, or pharmaceutically acceptable salt thereof exhibits an excellent effect on alleviating and/or treating pain. Therefore, another embodiment provides a pharmaceutical composition for alleviating and/or treating pain containing a phenyl carbamate compound represented by Chemical Formula 1; a racemate, an enantiomer, a diastereomer, a mixture of enantiomers, or a mixture of diastereomers thereof; or a pharmaceutically acceptable salt thereof, as an active ingredient.

Another embodiment provides a method of alleviating and/or treating pain comprising administering a therapeutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of alleviating and/or treating pain. The method may further comprise a step of identifying the subject in need of alleviating and/or treating pain prior to the step of administering. The term "therapeutically effective amount" may refer to an amount of the active gradient capable of exhibiting the effect of alleviating and/or treating pain.

Another embodiment provides a phenyl carbamate compound represented by Chemical Formula 1, a racemate, an enantiomer, a diastereomer, a mixture of enantiomers, or a mixture of diastereomers thereof, or a pharmaceutically acceptable salt thereof, for use in the alleviation and/or treatment of pain or in the manufacture of a medicament for alleviating and/or treating pain. Another embodiment provides a use of a phenyl carbamate compound represented by Chemical Formula 1, a racemate, an enantiomer, a diastereomer, a mixture of enantiomers, or a mixture of diastereomers thereof, or a pharmaceutically acceptable salt thereof, in the alleviation and/or treatment of pain or in the manufacture of a medicament for alleviating and/or treating pain.

The pain to be alleviated and/or treated in the present invention may include a nociceptive pain, psychogenic pain, inflammatory pain which is associated with tissue damage and the infiltration of immune cells, pathological pain which is a disease state caused by damage to the nervous system or by its abnormal function (dysfunctional pain, like in fibromyalgia, irritable bowel syndrome, tension type headache, etc.), and the like. Also, the pain may include a back pain, which is divided anatomically: neck pain, middle back pain, lower back pain or tailbone pain. Alternatively, the pain may include neuropathic pain, migraine, and the like. Neuropathic pain results from damage or disease affecting the somatosensory system. It may be associated with abnormal sensations called dysesthesia, and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching. Also, Migraine is a chronic disorder characterized by recurrent moderate to severe headaches often in association with a number of autonomic nervous system symptoms. The exact mechanisms of migraine are not known. The primary theory is related to increased excitability of the cerebral cortex and abnormal control of pain neurons in the trigeminal nucleus of the brainstem.

In a concrete embodiment, the pain may be one or more selected from the group consisting of neuropathic pain, cancer pain, postoperative pain, trigeminal neuralgia pain, idiopathic pain, diabetic neuropathic pain, migraine, and the like. In another concrete embodiment, the pain may not be a muscle spasm associated pain, such as muscle spasm associated lumbago.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like.

In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like.

Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the therapeutically effective amount of 0.01 to 750 mg/kg (body weight), preferably 0.1 to 500 mg/kg (body weight) per one day, based on the active ingredient. The therapeutically effective amount may be administered through oral or parenteral pathway, one or two or more times per one day.

The therapeutically effective amount and the administration pathway of the present pharmaceutical composition may be properly adjusted by a person skilled in the relevant field considering the conditions of the subject (patient), desired effects, and the like.

The subject may be a mammal including human or cells and/or tissues separated therefrom.

The phenyl carbamate compound of the present invention may prepared by the following reaction formula.

Reaction Formula I: Synthesis of Diol-1

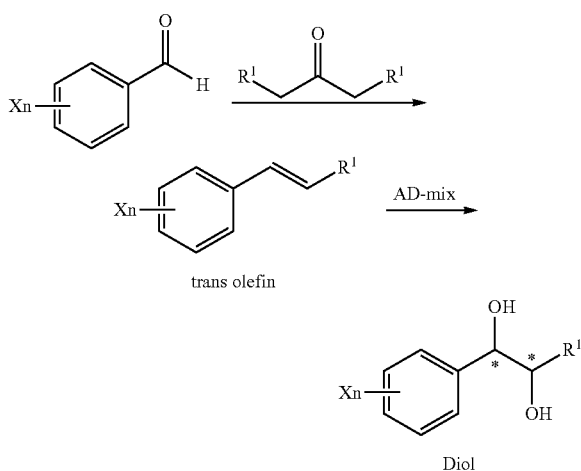

trans olefin

Diol

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

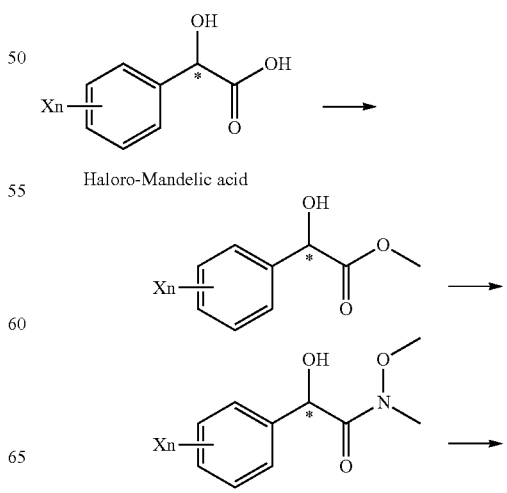

Haloro-Mandelic acid

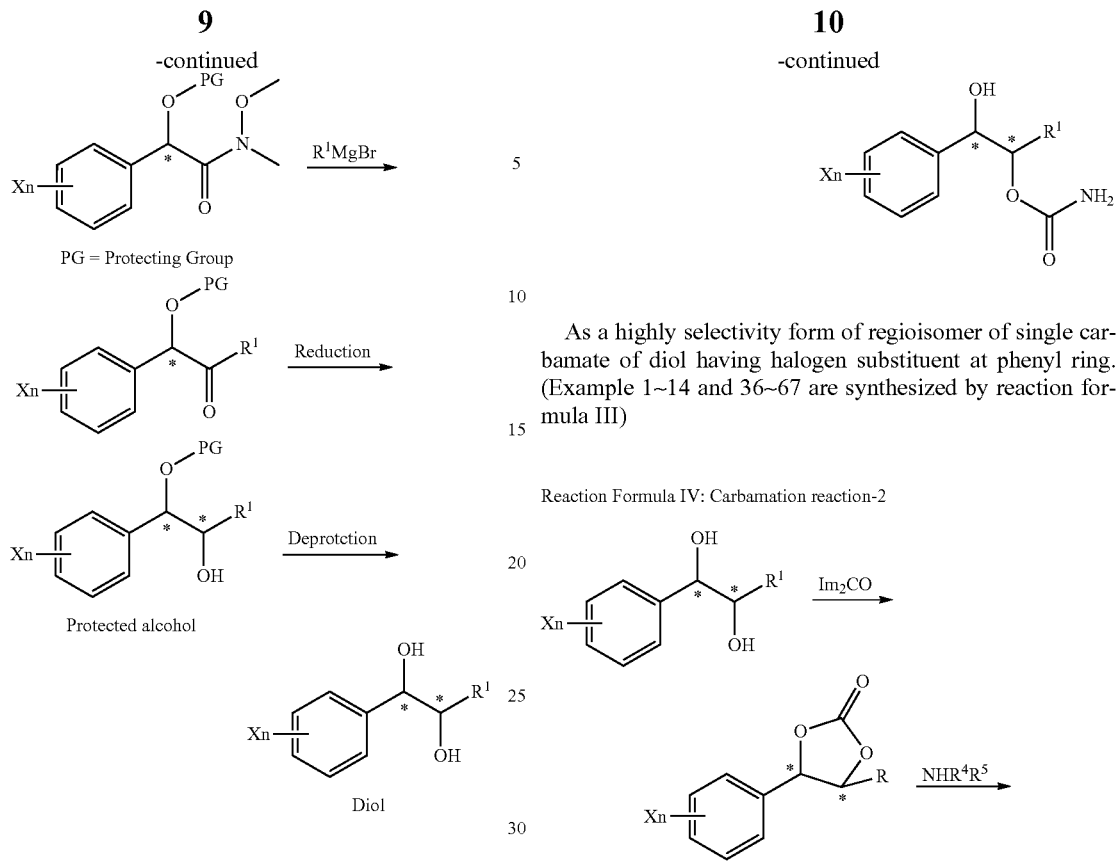

PG = Protecting Group

Protected alcohol

Diol

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

Reaction Formula III: Carbamation reaction-1

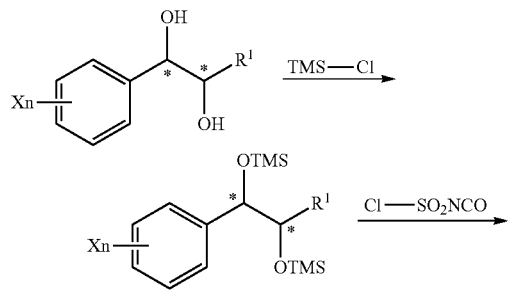

As a highly selectivity form of regioisomer of single carbamate of diol having halogen substituent at phenyl ring. (Example 1~14 and 36~67 are synthesized by reaction formula III)

Reaction Formula IV: Carbamation reaction-2

Two substances in the form of regioisomers of a single carbamate of diol having halogen substituent at phenyl ring may be separated by flash column chromatography to obtain two kinds of single carbamate compounds. (Example 15~35 and 68~115 are synthesized by reaction formula IV)

Reaction Formula V: Protection reaction

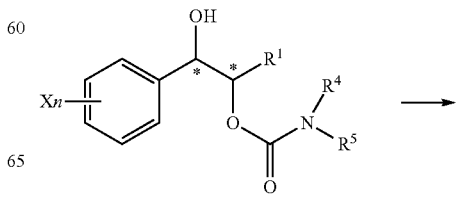

-continued

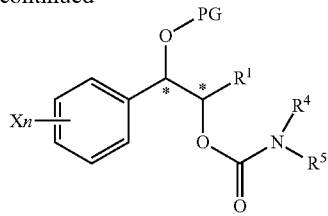

In the Reaction Formula V, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

In the Reaction Formula IV and V, R4 and R5 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R4 and R5 may be the same as or different from each other, and independently selected from the group consisting of hydrogen, methyl group, propyl group, isopropyl group, cyclopropyl group, cyclohexyl group, bicycloheptane group, and benzyl group.

Two substances in the form of regioisomers of a single carbamate of diol having halogen substituent at phenyl ring may be separated by flash column chromatography to obtain two kinds of single carbamate compounds.

EXAMPLE

Figure 1:
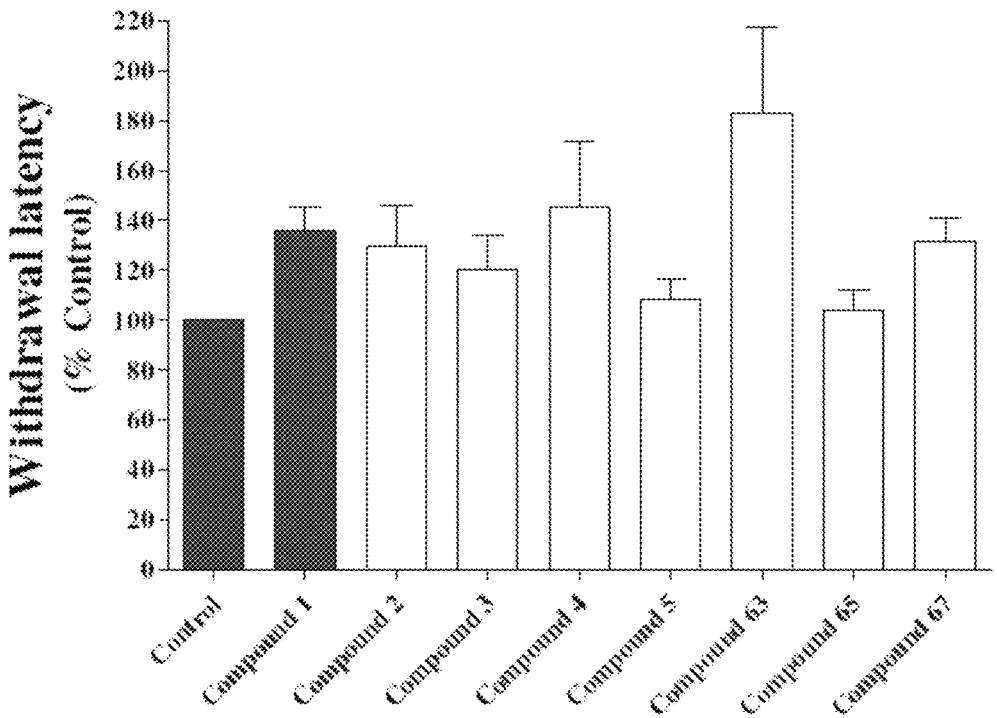
FIG. 1 is a graph showing withdrawal latency measured by hot-plate test for various phenyl carbamate compounds, wherein the value (% control) are expressed as the mean±S.E.M. (n=7~10), and statistic analysis was performed by One-way ANOVA at 0.5 hr: $F(8.78)=2.196$, $p<0.05$ (Turkey's test).

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

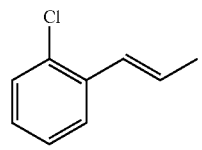

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1$H NMR (400 MHz, CDCl$_3$) δ1.94 (d, J=4.8 Hz, 3H), 6.24 (m, 1H), 6.78 (d, J=14 Hz, 1H), 7.11~7.51 (m, 4H)

Preparation Example 2

Synthesis of 1-(2-chlorophenyl)-trans-1-butene

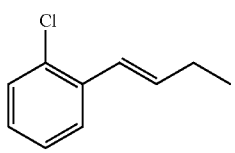

The substantially same method as described in Preparation Example 1 was conducted, except that 3-heptanone was used instead of 3-pentanone, to obtain the title compound (2.9 g, yield 83%).

$^1$H NMR (400 MHz, CDCl$_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.13~7.54 (m, 4H)

Preparation Example 3

Synthesis of 1-(2-chlorophenyl)-3-methyl-trans-1-butene

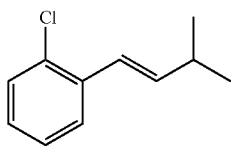

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.12~7.54 (m, 4H)

Preparation Example 4

Synthesis of 1-(2-chlorophenyl)-trans-1-hexene

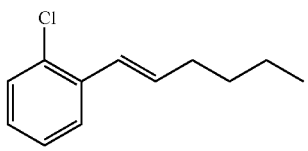

The substantially same method as described in Preparation Example 1 was conducted, except that 6-undecanone was used instead of 3-pentanone, to obtain the title compound (10 g, yield 85%).

$^1$H NMR (400 MHz, CDCl$_3$) δ0.96 (1, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.13~7.54 (m, 4H)

Preparation Example 5

Synthesis of 1-(2,4-dichlorophenyl)-trans-1-propene

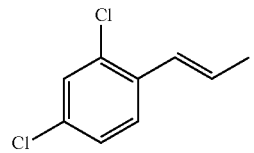

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 6

Synthesis of 1-(2,4-dichlorophenyl)-trans-1-butene

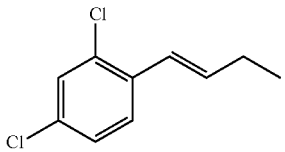

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ1.14 (d, J=7.6 Hz, 3H), 2.20~2.33 (m, 2H), 6.26 (dt, J=16 Hz, 6.8 Hz, 1H), 6.70 (d, J=15.6 Hz, 1H), 7.18~7.46 (m, 3H)

Preparation Example 7

Synthesis of 1-(2,6-dichlorophenyl)-3-methyl-trans-1-butene

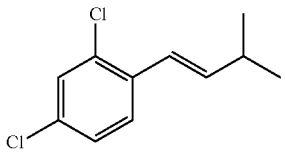

The substantially same method as described in Preparation Example 5 was conducted, except that 2,6-dimethyl-heptan-4-one was used instead of 3-pentanone, to obtain the title compound (0.23 g, yield 10~40%).

¹H NMR (400 MHz, CDCl₃) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.18~7.46 (m, 3H)

Preparation Example 8

Synthesis of 1-(2,4-dichlorophenyl)-trans-1-hexene

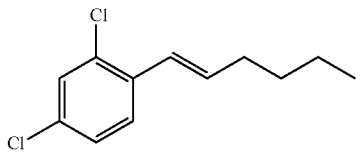

The substantially same method as described in Preparation Example 5 was conducted, except that 6-undecanone was used instead of 3-pentanone, to obtain the title compound (3.2 g, yield 40~80%).

¹H NMR (400 MHz, CDCl₃) δ0.96 (t, J=7.2 Hz, 3H), 1.38~1.52 (m, 4H), 2.25~2.31 (m, 2H), 6.22 (dt, J=15.6 Hz, 6.8 Hz, 1H), 6.70 (d, J=15.6 Hz, 1H), 7.18~7.46 (m, 3H)

Preparation Example 9

Synthesis of 1-(2,6-dichlorophenyl)-trans-1-propene

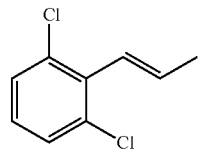

The substantially same method as described in Preparation Example 1 was conducted, except that 2,6-dichlorobenzenaldehyde was used instead of 2-chlorobenzenaldehyde, to obtain the title compound (0.4 g, yield 10~40%).

¹H NMR (400 MHz, CDCl₃) δ1.98 (d, J=8 Hz, 3H), 6.23~6.31 (m, 1H), 6.40 (d, J=16 Hz, 1H), 7.05~7.32 (m, 3H)

Preparation Example 10

Synthesis of 1-(2,6-dichlorophenyl)-trans-1-butene

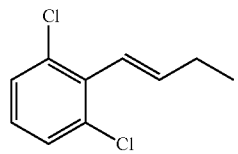

The substantially same method as described in Preparation Example 9 was conducted, except that 3-heptanone was used instead of 3-pentanone, to obtain the title compound (1.2 g, yield 10~40%).

¹H NMR (400 MHz, CDCl₃) δ1.17 (t, J=7.6 Hz, 3H), 2.30~2.37 (m, 2H), 6.29 (dt, J=16.4 Hz, 6 Hz, 1H), 6.37 (d, J=16.4 Hz, 1H), 7.05~7.32 (m, 3H)

Preparation Example 11

Synthesis of 1-(2,6-dichlorophenyl)-3-methyl-trans-1-butene

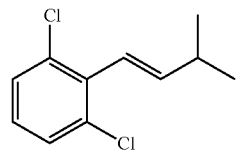

The substantially same method as described in Preparation Example 9 was conducted, except that 2,6-dimethyl-heptan-4-one was used instead of 3-pentanone, to obtain the title compound (0.23 g, yield 10~40%).

¹H NMR (400 MHz, CDCl₃) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.05~7.32 (m, 3H)

Preparation Example 12

Synthesis of 1-(2,6-dichlorophenyl)-trans-1-hexene

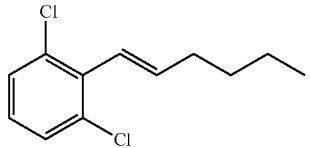

The substantially same method as described in Preparation Example 9 was conducted, except that 6-undecanone was used instead of 3-pentanone, to obtain the title compound (0.2 g, yield 10~40%).

¹H NMR (400 MHz, CDCl₃) δ0.99 (t, J=7.2 Hz, 3H), 1.14~1.59 (m, 4H), 2.30~2.36 (m, 2H), 6.24 (dt, J=16 Hz, 6.6 Hz, 1H), 6.38 (d, J=16.4 Hz, 1H), 7.05~7.33 (m, 3H)

Preparation Example 13

Synthesis of 1-(2,3-dichlorophenyl)-trans-1-propene

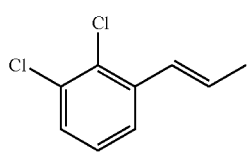

The substantially same method as described in Preparation Example 1 was conducted, except that 2,3-dichlorobenzenaldehyde was used instead of 2-chlorobenzenaldehyde, to obtain the title compound (0.2 g, yield 10~40%).

¹H NMR (400 MHz, CDCl₃) δ1.94 (d, J=4.8 Hz, 3H), 6.24 (m, 1H), 6.78 (d, J=14 Hz, 1H), 7.11~7.51 (m, 3H)

Preparation Example 14

Synthesis of 1-(2-chlorophenyl)-(S,S)-1,2-propanediol

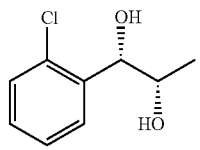

1-(2-chlorophenyl)-trans-1-propene (1.5 g, Preparation Example 1) was dissolved in 30 mL of the mixture of t-BuOH/H₂O (1:1 (V/V)). At 0° C., AD-mix-α (Aldrich, U.S.A.) (13.7 g) and methane sulfone amide (CH₃SO₂NH₂, 0.76 g, 0.0080 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (1.65 g, yield 90%).

¹H NMR (400 MHz, CDCl₃) δ1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H)

¹³CNMR (100 MHz, CDCl₃) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

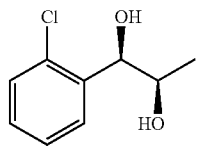

1-(2-chlorophenyl)-trans-1-propene (2.5 g, Preparation Example 1) was dissolved in 50 mL of the mixture of t-BuOH/H₂O (1:1 (V/V)). At 0° C., AD-mix-α (Aldrich, U.S.A.) (23.5 g) and methane sulfone amide (CH₃SO₂NH₂, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (2.96 g, yield 90%).

¹H NMR (400 MHz, CDCl₃) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 16

Synthesis of the mixture of 1-(2-chlorophenyl)-(S,S)-1,2-propanediol and 1-(2-chlorophenyl)-(R,R)-1,2-propanediol

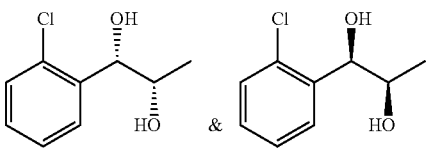

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concented under reduced pressure. The concentrated residue was purified by a silica gel column chromatography to produce the title compound (6.42 g, yield 80%).

¹H NMR (400 MHz, CDCl₃) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 17

Synthesis of 1-(2-chlorophenyl)-(S,S)-1,2-butanediol

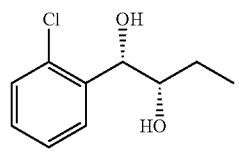

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

¹H NMR (400 MHz, CDCl₃) δ1.01 (1, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 18

Synthesis of 1-(2-chlorophenyl)-(R,R)-1,2-butanediol

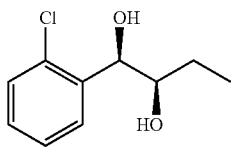

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR (400 MHz, CDCl$_3$) δ1.01 (1, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 19

Synthesis of the mixture of 1-(2-chlorophenyl)-(S,S)-1,2-butanediol and 1-(2-chlorophenyl)-(R,R)-1,2-butanediol

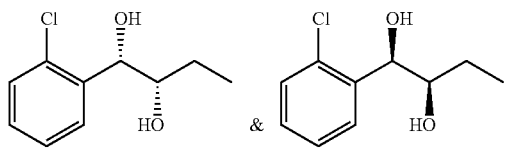

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR (400 MHz, CDCl$_3$) δ1.01 (1, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 20

Synthesis of 1-(2-chlorophenyl)-3-methyl-(S,S)-1,2-butanediol

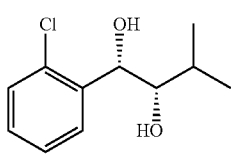

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR (400 MHz, CDCl$_3$) δ1.07 (1, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 21

Synthesis of 1-(2-chlorophenyl)-3-methyl-(R,R)-1,2-butanediol

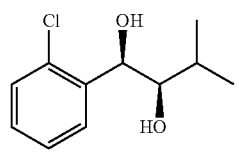

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR (400 MHz, CDCl$_3$) δ1.07 (t, J=7.2 Hz, 6H), 1.82~1.90 (m, 1H), 1.93 (d, J=5.6 Hz, 1H), 2.79 (d, J=6 Hz, 1H), 3.53~3.57 (m, 1H), 5.23~5.25 (m, 1H), 7.23~7.54 (m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

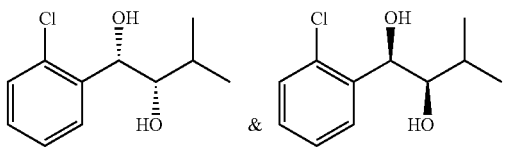

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

¹H NMR (400 MHz, CDCl₃) δ1.07 (1, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 23

Synthesis of 1-(2-chlorophenyl)-(S,S)-1,2-hexanediol

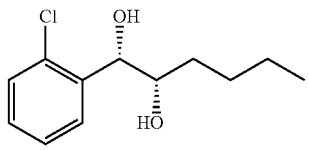

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).
¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H)

Preparation Example 24

Synthesis of 1-(2-chlorophenyl)-(R,R)-1,2-hexanediol

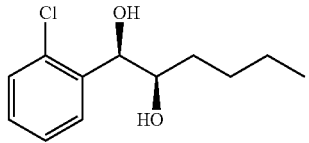

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
¹H NMR (400 MHz, CDCl₃) δ0.91 (1, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H)

Preparation Example 25

Synthesis of the mixture of 1-(2-chlorophenyl)-(S,S)-1,2-hexanediol and 1-(2-chlorophenyl)-(R,R)-1,2-hexanediol

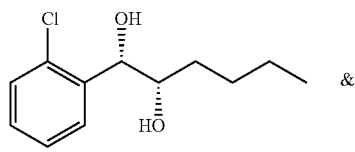

&

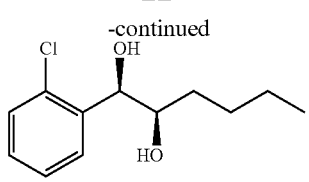

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).
¹H NMR (400 MHz, CDCl₃) δ0.90 (t, J=7.2 Hz, 3H), 1.26~1.55 (m, 6H), 2.08 (d, J=4.4 Hz, 1H), 2.71 (d, J=5.6 Hz, 1H), 3.78~3.84 (m, 1H), 5.04 (t, J=3.2 Hz, 1H), 7.24~7.55 (m, 4H)

Preparation Example 26

Synthesis of 1-(2,4-dichlorophenyl)-(S,S)-1,2-propanediol

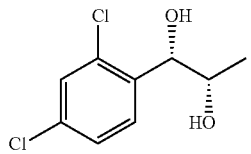

The substantially same method as described in Preparation Example 14 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.33 g, yield 60~95%).
¹H NMR (400 MHz, CDCl₃) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 27

Synthesis of 1-(2,4-dichlorophenyl)-(R,R)-1,2-propanediol

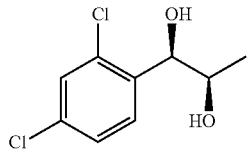

The substantially same method as described in Preparation Example 15 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

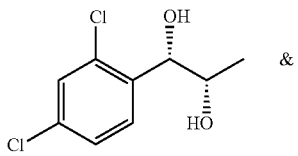 &

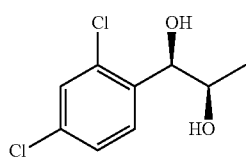

The substantially same method as described in Preparation Example 16 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 29

Synthesis of 1-(2,4-dichlorophenyl)-(S,S)-1,2-butanediol

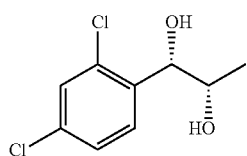

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR (400 MHz, CDCl$_3$) δ1.02 (1, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 30

Synthesis of 1-(2,4-dichlorophenyl)-(R,R)-1,2-butanediol

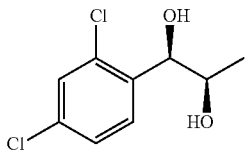

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR (400 MHz, CDCl$_3$) δ1.02 (1, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

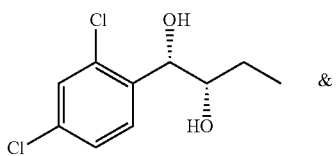 &

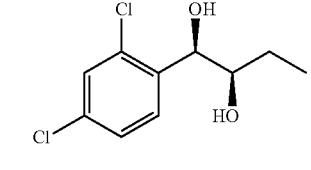

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

¹H NMR (400 MHz, CDCl₃) δ1.02 (1, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H)

Preparation Example 32

Synthesis of 1-(2,4-dichlorophenyl)-3-methyl-(S,S)-1,2-butanediol

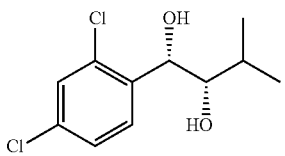

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 33

Synthesis of 1-(2,4-dichlorophenyl)-3-methyl-(R,R)-1,2-butanediol

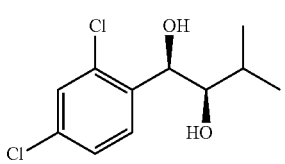

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

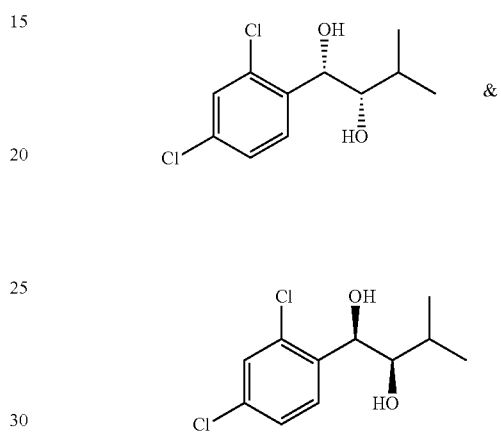

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 35

Synthesis of 1-(2,4-dichlorophenyl)-(S,S)-1,2-hexanediol

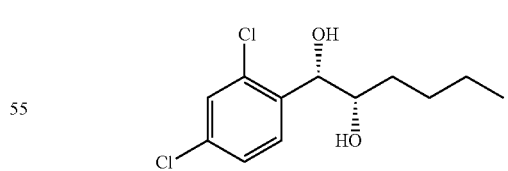

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 36

Synthesis of 1-(2,4-dichlorophenyl)-(R,R)-1,2-hexanediol

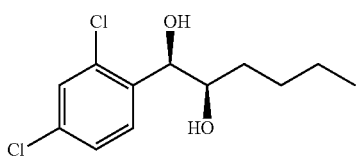

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

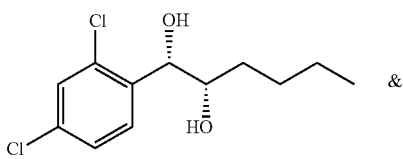
&
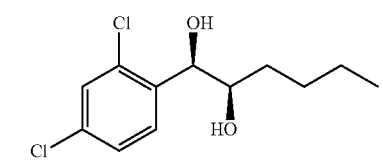 [SMILES: CCCC[C@@H](O)[C@H](O)c1ccc(Cl)cc1Cl]

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.21 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 38

Synthesis of 1-(2,6-dichlorophenyl)-(S,S)-1,2-propanediol

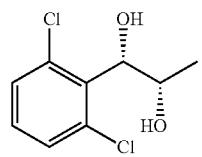

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 39

Synthesis of 1-(2,6-dichlorophenyl)-(R,R)-1,2-propanediol

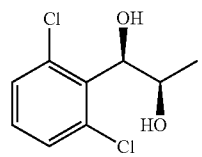

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

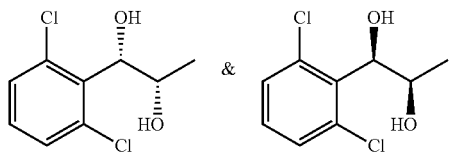

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 41

Synthesis of 1-(2,6-dichlorophenyl)-(S,S)-1,2-butanediol

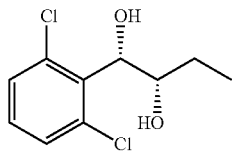

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 42

Synthesis of 1-(2,6-dichlorophenyl)-(R,R)-1,2-butanediol

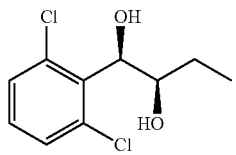

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

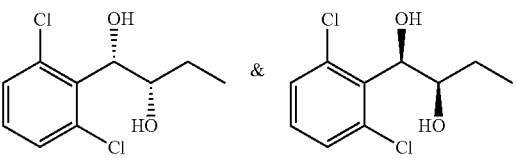

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 44

Synthesis of 1-(2,6-dichlorophenyl)-3-methyl-(S,S)-1,2-butanediol

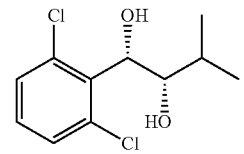

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 45

Synthesis of 1-(2,6-dichlorophenyl)-3-methyl-(R,R)-1,2-butanediol

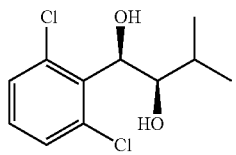

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

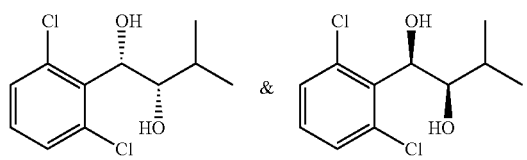

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 47

Synthesis of 1-(2,6-dichlorophenyl)-(S,S)-1,2-hexanediol

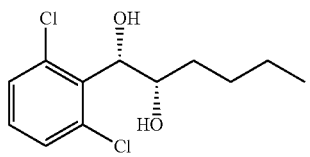 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 48

Synthesis of 1-(2,6-dichlorophenyl)-(R,R)-1,2-hexanediol

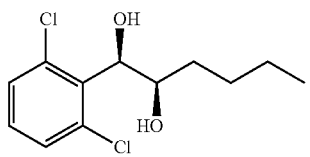 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

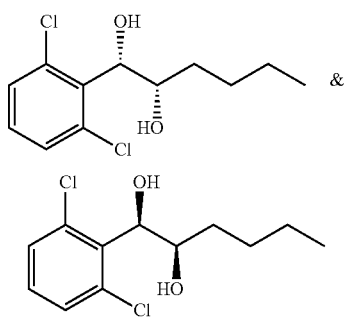

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 50

Synthesis of methyl 2-(2-chlorophenyl)-(R)-2-hydroxyacetate

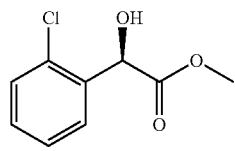

15 g of (R)-2-chloromandelic acid was mixed with methanol (CH₃OH, 150 ml) and phosphorus chloride oxide (POCl₃, 0.76 ml) in a flask by stiffing using a magnetic stirrer at the room temperature for 6 hours. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (15.64 g, yield 95%).

¹H NMR (400 MHz, CDCl₃) δ 3.59 (d, J=5.2, 1H), 3.79 (t, J=6.0, 3H), 5.59 (d, J=5.2, 1H), 7.28~7.43 (m, 4H)

Preparation Example 51

Synthesis of 2-(2-chlorophenyl)-(R)-2-hydroxy-N-methoxy-N-methylacetamide

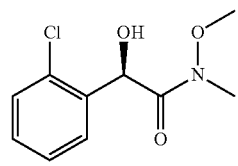

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO₄), filtrated, and concented under reduced pressure. The concentrated residue was purified by a silica gel column chromatography to produce the title compound (14.68 g, yield 82%).

¹H NMR (400 MHz, CDCl₃) δ3.23 (s, 3H), 3.28 (s, 3H), 4.33 (d, J=6.0 Hz, 1H), 5.81 (d, J=5.6 Hz, 1H), 7.23~7.42 (m, 4H)

Preparation Example 52

Synthesis of 2-(2-chlorophenyl)-N-methoxy-(R)-2-(t-butyl dimethlysiloxy)-N-methylacetamide

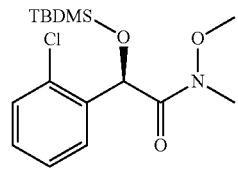

2-(2-chlorophenyl)-(R)-2-hydroxy-N-methoxy-N-methylacetamide (0.81 g, 3.52 mmol) obtained in Preparation Example 51 was dissolved in dichloromethane (DCM), and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with H₂O. The organic layer was separated and collected. The aqueous layer was extracted with CH₂Cl₂ (300 mL), dried over MgSO₄. Concentration under vacuum provided a title compound. (0.97 g, 80~95%).

¹H NMR (400 MHz, CDCl₃) δ−0.03 (s, 3H), 0.14 (s, 3H), 0.94 (s, 9H), 2.97 (s, 3H), 3.02 (s, 3H), 5.83 (s, 1H), 7.25~7.60 (m, 4H)

Preparation Example 53

Synthesis of 1-(2-chlorophenyl)-(R)-1-(t-butyldimethyl-siloxy)propane-2-on

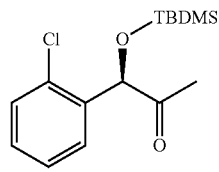

2-(2-chlorophenyl)-N-methoxy-(R)-2-(t-butyldimethylsiloxy)-N-methylacetamide (0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate (KHSO₄, 100 ml) and then, washed again with brine. The obtained organic layer was dehydrated with anhydrous magnesium sulfate (MgSO₄), filtrated, and concentrated under reduced pressure. The concentrated residue was purified by a silica gel column chromatography to produce the title compound (0.69 g, yield 85~95%).

¹H NMR (400 MHz, CDCl₃) δ−0.3 (s, 3H), 0.14 (s, 3H), 0.94 (s, 9H), 2.18 (s, 3H), 5.50 (s, 1H), 7.27~7.56 (m, 4H)

Preparation Example 54

Synthesis of 1-(2-chlorophenyl)-(R)-1-(t-butyldimethyl-siloxy)-(S)-2-propanol

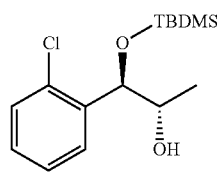

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride (Zn(BH₄)₂) was slowly added thereto and the obtained product was stirred. When the reaction was completed, the obtained product was washed by H₂O. The obtained organic layer was washed with H₂O, dehydrated with anhydrous magnesium sulfate (MgSO₄), filtrated, and concentrated under reduced pressure. The concentrated residue was purified by a silica gel column chromatography to produce the title compound (0.04 g, yield 25~33%, cis:trans=2:1).

¹H NMR (400 MHz, CDCl₃) δ−0.11 (s, 3H), 0.11 (s, 3H), 0.93 (S, 9H), 1.07 (d, J=6.4 3H), 2.05 (d, J=6.4 1H), 4.01~4.05 (m, 1H), 5.18 (d, J=4.0, 1H), 7.20~7.56 (m, 4H))

Preparation Example 55

Synthesis of 1-(2-chlorophenyl)-(R,S)-1,2-propanediol

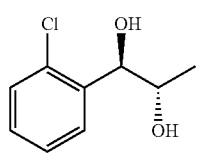

1-(2-chlorophenyl)-(R)-1-(t-butyldimethyl-siloxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concented under reduced pressure. The concentrated residue was purified by a silica gel column chromatography to produce the title compound (7.05 g, yield 60~90%).

¹H NMR (400 MHz, CDCl₃) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56

Synthesis of 1-(2-chlorophenyl)-(S,R)-1,2-propanediol

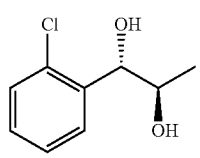

The substantially same method as described in Preparation Example 50~55 was conducted, except that (S)-2-chloromandelic acid was used instead of (R)-2-chloromandelic acid, to obtain the title compound (5.04 g, yield 84%).

¹H NMR (400 MHz, CDCl₃) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57

Synthesis of 1-(2,3-dichlorophenyl)-(S,S)-1,2-propanediol

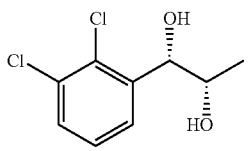

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).
¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 58

Synthesis of 1-(2,3-dichlorophenyl)-(R,R)-1,2-propanediol

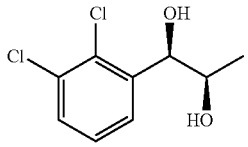

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).
¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

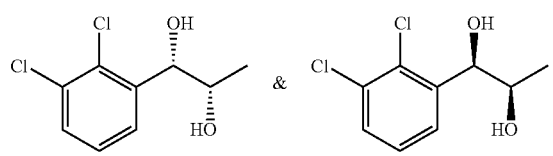

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).
¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 60

Synthesis of 1-(2-fluorophenyl)-trans-1-propene

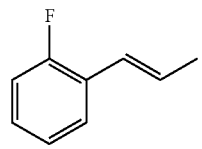

The substantially same method as described in Preparation Example 1 was conducted, except that 2-fluorobenzenaldehyde was used instead of 2-chlorobenzenealdehyde, to obtain the title compound (6.67 g, yield 61%).
¹H NMR (400 MHz, CDCl₃) δ1.94 (d, J=6.8 Hz, 3H), 6.30~6.38 (m, 1H), 6.57 (d, J=16 Hz, 1H), 7.00~7.41 (m, 4H)

Preparation Example 61

Synthesis of 1-(2-fluorophenyl)-(S,S)-1,2-propanediol

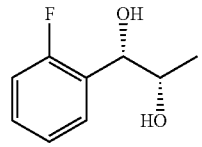

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).
¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 62

Synthesis of 1-(2-fluorophenyl)-(R,R)-1,2-propanediol

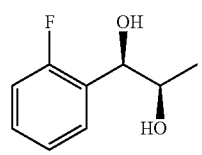

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 63

Synthesis of 2-iodobenzenealdehyde

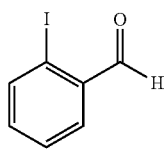

In a flask, 2-iodobenzyl alcohol (4 g, 17.09 mmol) was dissolved in dichloromethane (MC, 85 ml), and then, manganese oxide (MnO$_2$, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR (400 MHz, CDCl$_3$) δ7.30~7.99 (m, 4H), 10.10 (s, 1H)

Preparation Example 64

Synthesis of 1-(2-iodophenyl)-trans-1-propene

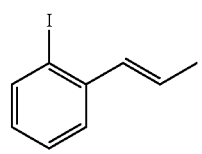

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR (400 MHz, CDCl$_3$) δ1.95 (dd, J=6.8 Hz, 1.6 Hz, 3H), 6.09~6.18 (m, 1H), 6.60 (dd, J=15.66 Hz, 1.8 Hz, 1H), 6.89~7.84 (m, 4H)

Preparation Example 65

Synthesis of 1-(2-iodophenyl)-trans-1-butene

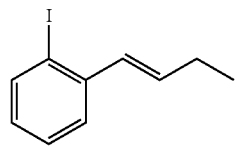

The substantially same method as described in Preparation Example 64 was conducted, except that 3-heptanone was used instead of 3-pentanone, to obtain the title compound (8.5 g, yield 75%).

$^1$H NMR (400 MHz, CDCl$_3$) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.89~7.85 (m, 4H)

Preparation Example 66

Synthesis of 1-(2-iodophenyl)-(S,S)-1,2-propanediol

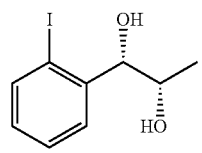

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400 MHz, CDCl$_3$) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H)

Preparation Example 67

Synthesis of 1-(2-iodophenyl)-(R,R)-1,2-propanediol

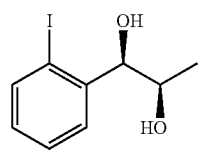

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

¹H NMR (400 MHz, CDCl₃) δ1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=5.0, 4.4 Hz, 1H), 7.00~7.87 (m, 4H)

Preparation Example 68

Synthesis of 1-(2-iodophenyl)-(S,S)-1,2-butanediol

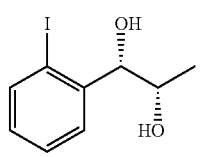

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 69

Preparation of 1-(2-chlorophenyl)-(S,S)-1,2-(Bis-trimethylsilanyloxy)propane

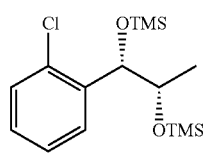

To a stirred solution of 1-(2-chlorophenyl)-(S,S)-1,2-propanediol (Preparation example 14, 67 g, 0.35 mol) in CH₂Cl₂ (670 ml) was added Et₃N (200 mL, 1.43 mol) and TMSCl (113.9 mL, 0.89 mol) at 0° C. under N₂. The reaction mixture was allowed to stir at 0° C. for 3 hr. The reaction mixture was quenched with H₂O (650 mL) at 0° C. The organic layer was separated and collected. The aqueous layer was extracted with CH₂Cl₂ (300 mL), dried over MgSO₄. Concentration under vacuum provided a crude product. 104.18 g (117.44%).

¹H NMR (400 MHz, CDCl₃) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.207~7.165 (m, 1H), 7.321~7.245 (m, 2H), 7.566~7.543 (m, 1H)

Preparation Example 70

Preparation of 1-(2-chlorophenyl)-(R,R)-1,2-(Bis-trimethylsilanyloxy)propane

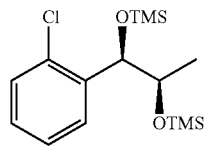

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

¹H NMR (400 MHz, CDCl₃) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 71

Preparation of 1-(2-chlorophenyl)-1,2-(Bis-trimethylsilanyloxy)propane

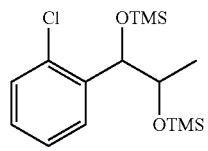

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).

¹H NMR (400 MHz, CDCl₃) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 72

Preparation of 1-(2-chlorophenyl)-(S,R)-1,2-(Bis-trimethylsilanyloxy)propane

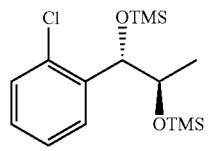

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).

¹H NMR (400 MHz, CDCl₃) δ–0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 73

Preparation of 1-(2-chlorophenyl)-(R,S)-1,2-(Bis-trimethylsilanyloxy)propane

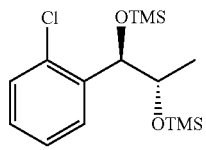

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).

¹H NMR (400 MHz, CDCl₃) δ–0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 74

Preparation of 1-(2-chlorophenyl)-(S,S)-1,2-(Bis-trimethylsilanyloxy)butane

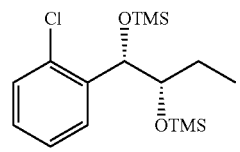

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).

¹H NMR (400 MHz, CDCl₃) δ–0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 75

Preparation of 1-(2-chlorophenyl)-(R,R)-1,2-(Bis-trimethylsilanyloxy)butane

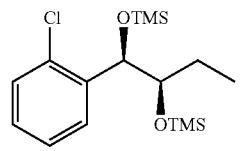

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).

¹H NMR (400 MHz, CDCl₃) δ–0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 76

Preparation of 1-(2-chlorophenyl)-1,2-(Bis-trimethylsilanyloxy)butane

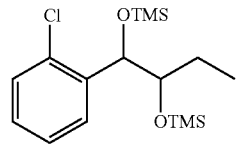

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).

¹H NMR (400 MHz, CDCl₃) δ–0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 77

Preparation of 1-(2-chlorophenyl)-3-methyl-(S,S)-1,2-(Bis-trimethylsilanyloxy)-butane

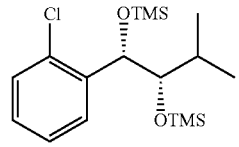

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%).

$^1$H NMR (400 MHz, CDCl$_3$) δ−0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 78

Preparation of 1-(2-chlorophenyl)-3-methyl-(R,R)-1, 2-(Bis-trimethylsilanyloxy)-butane

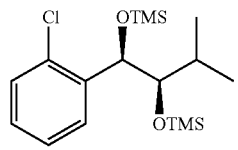

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

$^1$H NMR (400 MHz, CDCl$_3$) δ−0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 79

Preparation of 1-(2-chlorophenyl)-3-methyl-1,2-(Bis-trimethylsilanyloxy)-butane

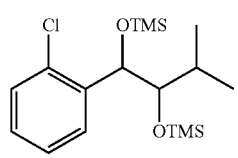

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ−0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 80

Preparation of 1-(2-chlorophenyl)-(S,S)-1,2-(Bis-trimethylsilanyloxy)-hexane

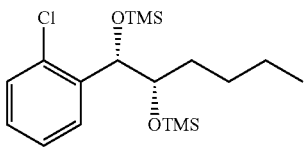

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 81

Preparation of 1-(2-chlorophenyl)-(S,S)-1,2-(Bis-trimethylsilanyloxy)-hexane

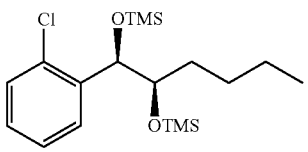

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 82

Preparation of 1-(2-chlorophenyl)-(S,S)-1,2-(Bis-trimethylsilanyloxy)-hexane

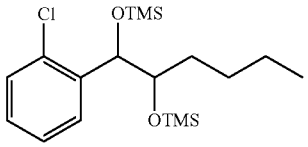

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).

$^1$H NMR (400 MHz, CDCl$_3$) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 83

Preparation of 1-(2,4-dichlorophenyl)-(S,S)-1,2-(Bis-trimethylsilanyloxy)-propane

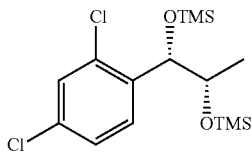

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).

$^1$H NMR (400 MHz, CDCl$_3$) δ−0.053 (s, 9H), 0.044 (s, 9H), 1.22 (d, J=6.4 Hz, 3H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 84

Preparation of 1-(2,6-dichlorophenyl)-(S,S)-1,2-(Bis-trimethylsilanyloxy)-propane

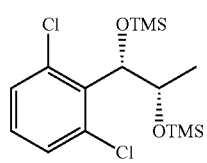

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.13~7.36 (m, 3H)

Preparation Example 85

Preparation of 1-(2,3-dichlorophenyl)-(S,S)-1,2-(Bis-trimethylsilanyloxy)-propane

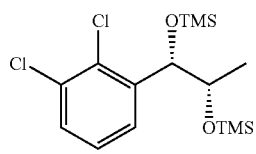

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 86

Preparation of 1-(2,4-dichlorophenyl)-(S,S)-1,2-(Bis-trimethylsilanyloxy)-butane

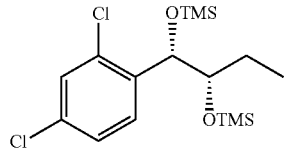

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 87

Preparation of 1-(2,6-dichlorophenyl)-(S,S)-1,2-(Bis-trimethylsilanyloxy)-butane

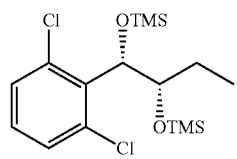

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

¹H NMR (400 MHz, CDCl₃) δ−0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 88

Preparation of 1-(2,4-dichlorophenyl)-3-methyl-(S,S)-1,2-(Bis-trimethylsilanyloxy)-butane

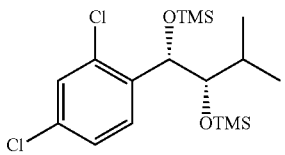

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

¹H NMR (400 MHz, CDCl₃) δ−0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 89

Preparation of 1-(2,6-dichlorophenyl)-3-methyl-(S,S)-1,2-(Bis-trimethylsilanyloxy)-butane

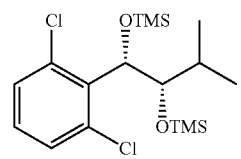

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

¹H NMR (400 MHz, CDCl₃) δ−0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 90

Preparation of 1-(2,4-dichlorophenyl)-(S,S)-1,2-(Bis-trimethylsilanyloxy)-hexane

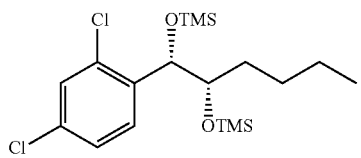

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

¹H NMR (400 MHz, CDCl₃) δ−0.053 (s, 9H), 0.044 (s, 9H), 0.89~0.93 (m, 3H), 1.30~1.39 (m, 2H), 1.49~1.52 (m, 2H), 1.56~1.6 (m, 2H), 3.72~3.77 (m, 1H), 4.98 (t, J=4.8 Hz, 1H), 7.28~7.50 (m, 3H)

Preparation Example 91

Preparation of 1-(2,6-dichlorophenyl)-(S,S)-1,2-(Bis-trimethylsilanyloxy)-hexane

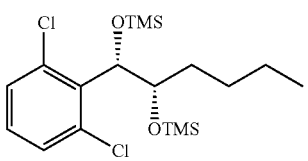

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

¹H NMR (400 MHz, CDCl₃) δ−0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 92

Preparation of 1-(2,4-dichlorophenyl)-(R,R)-1,2-(Bis-trimethylsilanyloxy)-propane

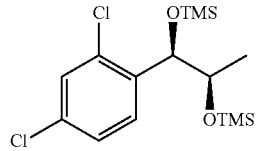

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

¹H NMR (400 MHz, CDCl₃) δ−0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 93

Preparation of 1-(2,6-dichlorophenyl)-(R,R)-1,2-(Bis-trimethylsilanyloxy)-propane

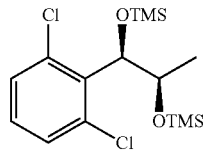

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

¹H NMR (400 MHz, CDCl₃) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 94

Preparation of 1-(2,3-dichlorophenyl)-(R,R)-1,2-(Bis-trimethylsilanyloxy)-propane

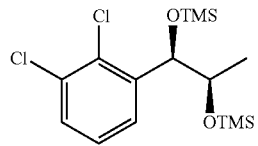

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

¹H NMR (400 MHz, CDCl₃) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 95

Preparation of 1-(2,4-dichlorophenyl)-(R,R)-1,2-(Bis-trimethylsilanyloxy)-butane

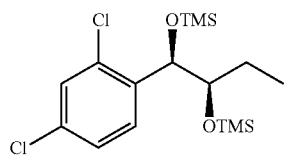

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

¹H NMR (400 MHz, CDCl₃) δ−0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 96

Preparation of 1-(2,6-dichlorophenyl)-(R,R)-1,2-(Bis-trimethylsilanyloxy)-butane

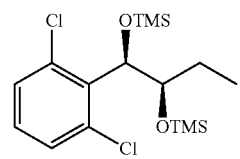

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

¹H NMR (400 MHz, CDCl₃) δ–0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 97

Preparation of 1-(2,4-dichlorophenyl)-3-methyl-(R,R)-1,2-(Bis-trimethylsilanyloxy)-butane

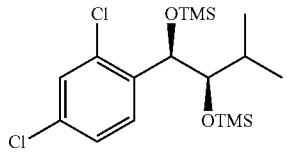

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).
¹H NMR (400 MHz, CDCl₃) δ–0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 98

Preparation of 1-(2,6-dichlorophenyl)-3-methyl-(R,R)-1,2-(Bis-trimethylsilanyloxy)-butane

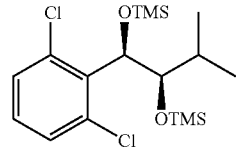

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).
¹H NMR (400 MHz, CDCl₃) δ–0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 99

Preparation of 1-(2,4-dichlorophenyl)-(R,R)-1,2-(Bis-trimethylsilanyloxy)-hexane

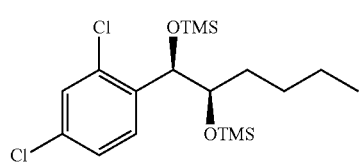

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).
¹H NMR (400 MHz, CDCl₃) δ–0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8 Hz, 1H), 7.28~7.50 (m, 3H)

Preparation Example 100

Preparation of 1-(2,6-dichlorophenyl)-(R,R)-1,2-(Bis-trimethylsilanyloxy)-hexane

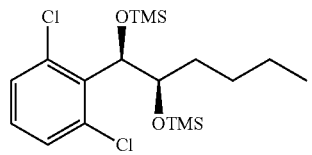

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).
¹H NMR (400 MHz, CDCl₃) δ–0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 101

Preparation of 1-(2,4-dichlorophenyl)-1,2-(Bis-trimethylsilanyloxy)-propane

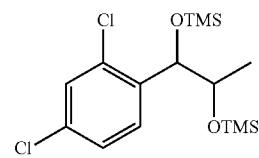

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ−0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 102

Preparation of 1-(2,6-dichlorophenyl)-1,2-(Bis-trimethylsilanyloxy)-propane

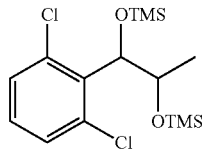

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 103

Preparation of 1-(2,3-dichlorophenyl)-1,2-(Bis-trimethylsilanyloxy)-propane

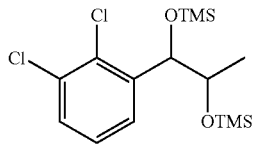

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 104

Preparation of 1-(2,4-dichlorophenyl)-1,2-(Bis-trimethylsilanyloxy)-butane

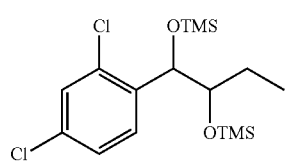

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

$^1$H NMR (400 MHz, CDCl$_3$) δ−0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 105

Preparation of 1-(2,6-dichlorophenyl)-1,2-(Bis-trimethylsilanyloxy)-butane

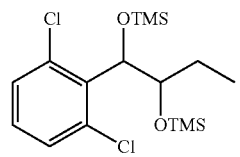

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 106

Preparation of 1-(2,4-dichlorophenyl)-3-methyl-1,2-(Bis-trimethylsilanyloxy)-butane

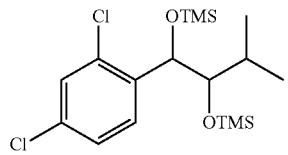

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).

¹H NMR (400 MHz, CDCl₃) δ−0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 107

Preparation of 1(2,6-dichlorophenyl)-3-methyl-1,2-(Bis-trimethylsilanyloxy)-butane

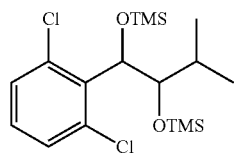

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).

¹H NMR (400 MHz, CDCl₃) δ−0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 108

Preparation of 1-(2,4-dichlorophenyl)-1,2-(Bis-trimethylsilanyloxy)-hexane

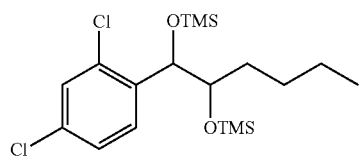

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

¹H NMR (400 MHz, CDCl₃) δ−0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8 Hz, 1H), 7.28~7.50 (m, 3H)

Preparation Example 109

Preparation of 1-(2,6-dichlorophenyl)-1,2-(Bis-trimethylsilanyloxy)-hexane

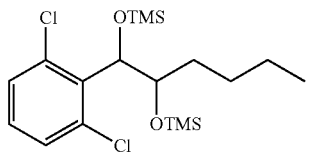

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

¹H NMR (400 MHz, CDCl₃) δ−0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 110

Preparation of 1-(2-fluoroophenyl)-(S,S)-1,2-(Bis-trimethylsilanyloxy)-propane

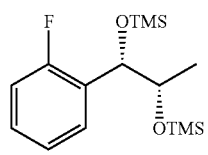

The substantially same method as described in Preparation Example 69 was conducted, except that 1-(2-fluoroophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

¹H NMR (400 MHz, CDCl₃) δ−0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 111

Preparation of 1-(2-fulorophenyl)-(R,R)-1,2-(Bis-trimethylsilanyloxy)-propane

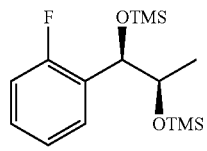

The substantially same method as described in Preparation Example 69 was conducted, except that 1-(2-fluoroophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

¹H NMR (400 MHz, CDCl₃) δ−0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 112

Preparation of 1-(2-iodophenyl)-(S,S)-1,2-(Bis-trimethylsilanyloxy)-propane

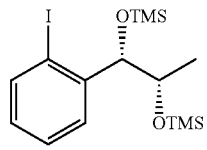

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

¹H NMR (400 MHz, CDCl₃) δ−0.053 (s, 9H), 0.044 (s, 9H), 1.27 (d, J=6.4 Hz, 3H), 3.99 (t, J=6.0 Hz, 1H), 4.81 (d, J=4.0 Hz, 1H), 7.01~7.87 (m, 4H)

Preparation Example 113

Preparation of 1-(2-iodophenyl)-(R,R)-1,2-(Bis-trimethylsilanyloxy)-propane

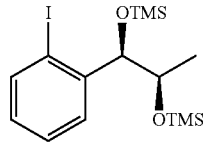

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

¹H NMR (400 MHz, CDCl₃) δ−0.053 (s, 9H), 0.044 (s, 9H), 1.26 (d, J=6.4 Hz, 3H), 3.98 (t, J=6.2 Hz, 1H), 4.88 (d, J=4.4 Hz, 1H), 7.00~7.87 (m, 4H)

Preparation Example 114

Preparation of 1-(2-iodophenyl)-(S,S)-1,2-(Bis-trimethylsilanyloxy)-butane

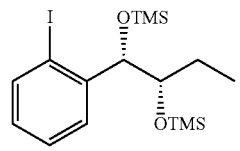

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

¹H NMR (400 MHz, CDCl₃) δ−0.053 (s, 9H), 0.044 (s, 9H), 1.04 (t, J=7.6 Hz, 3H), 1.60~1.71 (m, 2H), 3.71~3.76 (m, 1H), 4.87 (d, J=4.8 Hz, 1H), 7.01~7.87 (m, 4H)

Example 1

Preparation of 1-(2-chlorophenyl)-(S)-1-hydroxypropyl-(S)-2-carbamate (1)

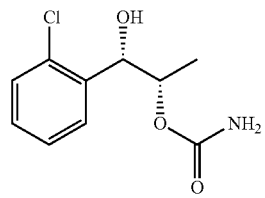

To a stirred solution of crude 1-(2-chlorophenyl)-(S,S)-1,2-(Bis-trimethylsilanyloxy)propane (preparation example 69, 104 g, 0.31 mol) in toluene (670 mL) was added by Chlorosulfonyl isocynate (62.5 mL, 0.71 mol) at 0° C. The reaction mixture was stirred for 2 hr. The reaction mixture was quenched with ice water and then was stirred by additional cold H₂O (500 mL) for 2 hr. After separation of organic layer, the aqueous was adjusted pH2~3 with sat. NaHCO₃ (400 mL) and extracted with EtOAc (300 mL×3). The EtOAc layer was washed with sat. NaHCO₃ (500 mL) and H₂O (500 mL). The organic phase was treated with Charcol for 1.5 hr. The organic phase was filtered with Cellite, dreid over MgSO₄. Filterion and concentration under vacuum provided the title compound of white solid (yield 85% (71.1 g), ee=99.9% MP=83~84° C., [α]$_D$=+57.8 (c=0.25, MeOH))

¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

$^{13}$C NMR (100 MHz, CDCl$_3$) δ16.4, 73.1, 75.0, 127.0, 128.4, 129.1, 129.5, 132.7, 138.0, 156.6

Example 2

Preparation of 1-(2-chlorophenyl)-(R)-1-hydroxypropyl-(R)-2-carbamate (2)

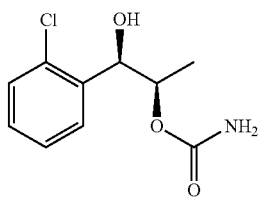

The substantially same method as described in Example 1 was conducted, except that 1-(2-chlorophenyl)-(R,R)-1,2-(Bis-trimethylsilanyloxy)propane (Preparation example 70) was used instead of 1-(2-chlorophenyl)-(S,S)-1,2-(Bis-trimethylsilanyloxy)propane (Preparation example 69) to obtain the title compound (5.7 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 3

Preparation of 1-(2-chlorophenyl)-1-hydroxypropyl-2-carbamate (3)

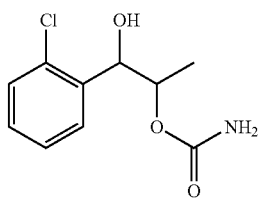

The substantially same method as described in Example 1 was conducted, except that 1-(2-chlorophenyl)-1,2-(Bis-trimethylsilanyloxy)propane (Preparation example 71) was used instead of 1-(2-chlorophenyl)-(S,S)-1,2-(Bis-trimethylsilanyloxy)propane (Preparation example 69) to obtain the title compound (3.8 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 4

Preparation of 1-(2-chlorophenyl)-(S)-1-hydroxypropyl-(R)-2-carbamate (4)

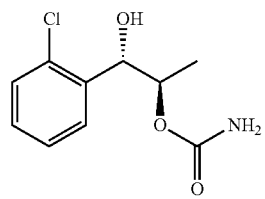

The substantially same method as described in Example 1 was conducted, except that 1-(2-chlorophenyl)-(S,R)-1,2-(Bis-trimethylsilanyloxy)propane (Preparation example 72) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 5

Preparation of 1-(2-chlorophenyl)-(R)-1-hydroxypropyl-(S)-2-carbamate (5)

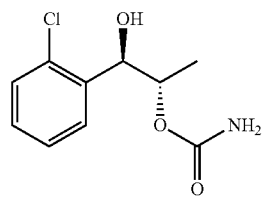

The substantially same method as described in Example 1 was conducted, except that 1-(2-chlorophenyl)-(R,S)-1,2-(Bis-trimethylsilanyloxy)propane (Preparation example 73) was used instead of 1-(2-chlorophenyl)-(S,S)-1,2-(Bis-trimethylsilanyloxy)propane (Preparation example 69) to obtain the title compound (2.3 g, yield 60~90%).

¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 6

Preparation of 1-(2-chlorophenyl)-(S)-1-hydroxybutyl-(S)-2-carbamate (6)

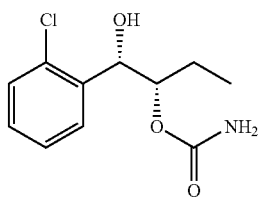

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy)propane (Preparation example 69) to obtain the title compound (2.6 g, yield 60~90%).

¹H NMR (400 MHz, CDCl₃) δ0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H)

Example 7

Synthesis of 1-(2-chlorophenyl)-(R)-1-hydroxybtyl-(R)-2-carbamate (7)

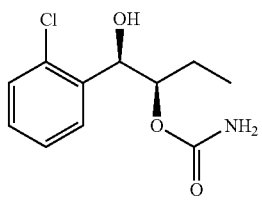 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy)propane (Preparation example 69) to obtain the title compound (2.5 g, yield 60~90%).

¹H NMR (400 MHz, CDCl₃) δ 0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H)

Example 8

Synthesis of 1-(2-chlorophenyl)-1-hydroxybutyl-2-carbamate (8)

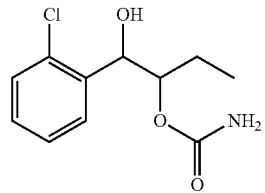 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy)propane (Preparation example 69) to obtain the title compound (1.9 g, yield 60~90%).

¹H NMR (400 MHz, CDCl₃) δ 0.97 (t, J=7 Hz, 3H), 1.58~1.74 (m, 2H), 2.94 (d, J=6 Hz, 1H), 4.69 (br s, 2H), 4.94~4.99 (m, 1H), 5.24 (t, J=6 Hz, 1H), 7.23~7.56 (m, 4H)

Example 9

Synthesis of 1-(2-chlorophenyl)-(S)-1-hydroxy-3-methyl-butyl-(S)-2-carbamate (9)

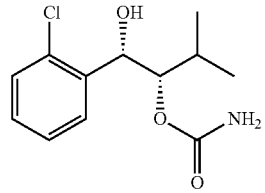 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy)propane (Preparation example 69) to obtain the title compound (1.7 g, yield 60~90%).

¹H NMR (400 MHz, CDCl₃) δ1.01 (d, J=6.4 Hz, 3H), 1.09 (d, J=6.8 Hz, 3H), 2.06 (m, 1H), 2.75 (d, J=6.8 Hz, 1H), 4.58

(br s, 2H), 4.85~4.88 (m, 1H), 5.34~5.37 (m, 1H), 7.22~7.33 (m, 2H), 7.35~7.37 (m, 1H), 7.51~7.53 (m, 1H)

Example 10

Synthesis of 1-(2-chlorophenyl)-(R)-1-hydroxy-3-methyl-butyl-(R)-2-carbamate (10)

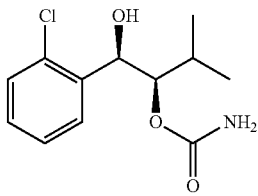 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR (400 MHz, CDCl$_3$) δ1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H)

Example 11

Synthesis of 1-(2-chlorophenyl)-1-hydroxy-3-methyl-butyl-2-carbamate (11)

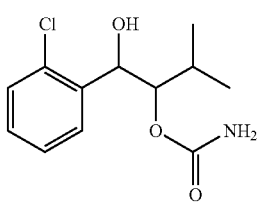 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.00 (d, J=6.4 Hz, 3H), 1.09 (d, J=6.4 Hz, 3H), 2.08 (m, 1H), 2.76 (d, J=6.0 Hz, 1H), 4.59 (br s, 2H), 4.87 (dd, J=7.2 Hz, 4.4 Hz, 1H), 5.36 (t, J=4.6, 1H), 7.23~7.54 (m, 4H)

Example 12

Synthesis of 1-(2-chlorophenyl)-(S)-1-hydroxy-hexyl-(S)-2-carbamate (12)

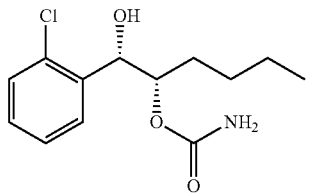 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR (400 MHz, CDCl$_3$) δ0.88 (t, J=7 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H)

Example 13

Synthesis of 1-(2-chlorophenyl)-(R)-1-hydroxy-hexyl-(R)-2-carbamate (13)

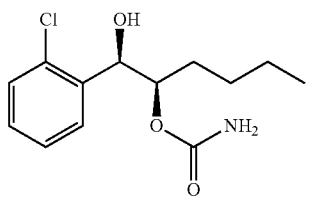 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR (400 MHz, CDCl$_3$) δ 0.89 (dd, J=5 Hz, 3H), 1.28~1.43 (m, 4H), 1.52~1.58 (m, 1H), 1.65~1.72 (m, 1H), 2.90 (d, J=6 Hz, 1H), 4.64 (br s, 2H), 5.01~5.06 (m, 1H), 5.22 (t, J=6 Hz, 1H), 7.22~7.56 (m, 4H)

Example 14

Synthesis of 1-(2-chlorophenyl)-1-hydroxyhexyl-2-carbamate (14)

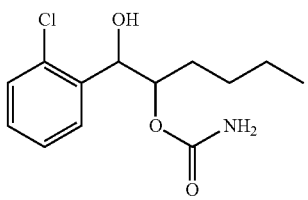 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy)propane (Preparation example 69) to obtain the title compound (2.1 g, yield 60~90%).

¹H NMR (400 MHz, CDCl₃) δ 0.88 (dd, J=5 Hz, 3H), 1.31~1.43 (m, 4H), 1.63~1.70 (m, 1H), 1.52~1.60 (m, 1H), 3.06 (d, J=6 Hz, 1H), 4.75 (br s, 2H), 5.00~5.05 (m, 1H), 5.21 (t, J=6 Hz, 1H), 7.22~7.55 (m, 4H)

Example 15

Synthesis of 1-(2-chlorophenyl)-(S)-1-hydroxypropyl-(S)-2-N-methylcarbamate (15)

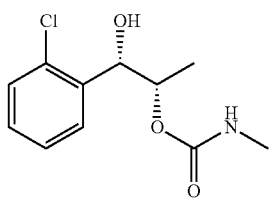 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH₃NH₂, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO₄), filtrated, and concented under reduced pressure. The concentrated residue was purified by a silica gel column chromatography, to obtain the title compound (1.6 g, yield 51%).

¹H NMR (400 MHz, CDCl₃) δ1.03~1.25 (m, 3H), 2.76 (s, 3H), 3.34 (s, 1H), 4.80 (br s 1H), 5.04 (t, J=12.5 Hz, 1H), 5.14 (s, 1H), 7.20~7.53 (m, 4H)

Example 16

Synthesis of 1-(2-chlorophenyl)-(S)-1-hydroxypropyl-(S)-2-N-propylcarbamate (16)

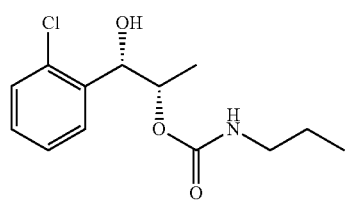 [SMILES: CCCNC(=O)O[C@@H](C)[C@@H](O)c1ccccc1Cl]

The substantially same method as described in Example 15 was conducted, except that propylamine was used instead of methylamine solution (CH₃NH₂ in EtOH), to obtain the title compound (0.79 g, yield 25%).

¹H NMR (400 MHz, CDCl₃) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.22~7.53 (m, 4H)

Example 17

Synthesis of 1-(2-chlorophenyl)-(S)-1-hydroxypropyl-(S)-2-N-isopropylcarbamate (17)

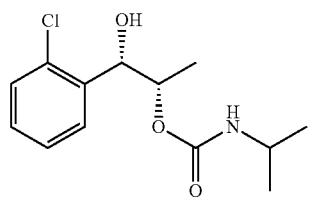

The substantially same method as described in Example 15 was conducted, except that isopropylamine was used instead of methylamine solution (CH₃NH₂ in EtOH), to obtain the title compound (1.5 g, yield 41%).

¹H NMR (400 MHz, CDCl₃) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.20~7.53 (m, 4H)

Example 18

Synthesis of 1-(2-chlorophenyl)-(S)-1-hydroxypropyl-(S)-2-N-cyclopropylcarbamate (18)

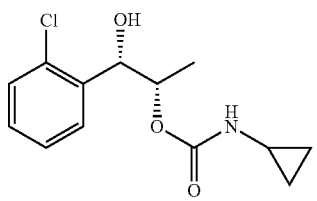 [SMILES: C[C@H](OC(=O)NC1CC1)[C@@H](O)c1ccccc1Cl]

The substantially same method as described in Example 15 was conducted, except that cyclopropylamine was used instead of methylamine solution (CH₃NH₂ in EtOH), to obtain the title compound (2.2 g, yield 43%).

¹H NMR (400 MHz, CDCl₃) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H)

Example 19

Synthesis of 1-(2-chlorophenyl)-(S)-1-hydroxypropyl-(S)-2-N-cyclohexyl carbamate (19)

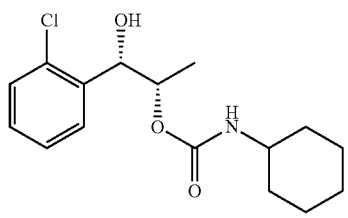 [SMILES: C[C@H](OC(=O)NC1CCCCC1)[C@@H](O)c1ccccc1Cl]

The substantially same method as described in Example 15 was conducted, except that cyclohexylamine was used instead of methylamine solution (CH₃NH₂ in EtOH), to obtain the title compound (1.1 g, yield 26%).

¹H NMR (400 MHz, CDCl₃) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.20~7.53 (m, 4H)

Example 20

Synthesis of 1-(2-chlorophenyl)-(S)-1-hydroxypropyl-(S)-2-N-benzyl carbamate (20)

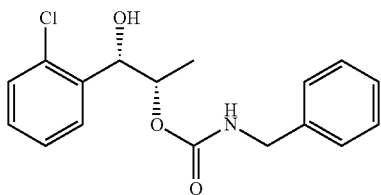 [SMILES: C[C@H](OC(=O)NCc1ccccc1)[C@@H](O)c1ccccc1Cl]

The substantially same method as described in Example 15 was conducted, except that benzylamine was used instead of methylamine solution (CH₃NH₂ in EtOH), to obtain the title compound (1.2 g, yield 18%).

¹H NMR (400 MHz, CDCl₃) δ 1.27 (d, J=10 Hz, 3H), 3.12 (d, J=5 Hz, 1H), 4.37 (d, J=6 Hz, 2H), 5.12~5.19 (m, 3H), 7.15~7.56 (m, 9H)

Example 21

Synthesis of 1-(2-chlorophenyl)-(S)-1-hydroxypropyl-(S)-2-N-bicyclo[2,2,1]heptanescarbamate (21)

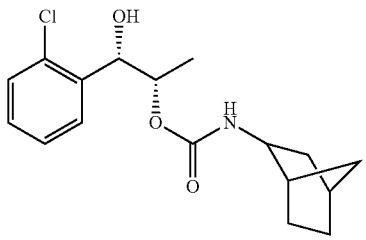

The substantially same method as described in Example 15 was conducted, except that 2-aminonorbornane was used instead of methylamine solution (CH₃NH₂ in EtOH), to obtain the title compound (1.7 g, yield 32%).

¹H NMR (400 MHz, CDCl₃) δ108~1.35 (m, 9H), 1.65 (br s, 1H), 1.75~1.71 (m, 1H), 2.14~2.24 (m, 1H), 2.27~2.30 (m,

1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 22

Synthesis of 1-(2-chlorophenyl)-(R)-1-hydroxypropyl-(R)-2-N-methylcarbamate (22)

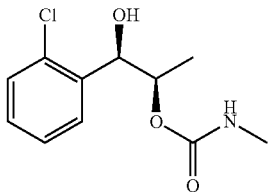 [SMILES: CNC(=O)O[C@H](C)[C@H](O)c1ccccc1Cl]

The substantially same method as described in Example 15 was conducted, except that 1-(2-chlorophenyl)-(R,R)-1,2-propanediol (Preparation example 15) was used instead of 1-(2-chlorophenyl)-(S,S)-1,2-propanediol (Preparation example 14), to obtain the title compound (3.36 g, yield 60%).

$^1$H NMR (400 MHz, CDCl$_3$) δ 1.20 (d, J=6.8 Hz, 3H), 2.80 (d, J=4.8 Hz, 3H), 3.20 (d, J=4.4 Hz, 1H), 4.75 (br s, 1H), 5.03~5.09 (m, 1H), 5.14~5.17 (m, 1H), 7.22~7.55 (m, 4H)

Example 23

Synthesis of 1-(2-chlorophenyl)-(R)-1-hydroxypropyl-(R)-2-N-propylcarbamate (23)

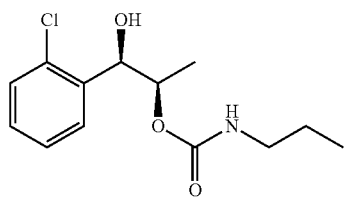 [SMILES: CCCNC(=O)O[C@H](C)[C@H](O)c1ccccc1Cl]

The substantially same method as described in Example 22 was conducted, except that propylamine was used instead of methylamine solution (CH$_3$NH$_2$ in EtOH), to obtain the title compound (3.1 g, yield 53%).

$^1$H NMR (400 MHz, CDCl$_3$) δ 0.92 (t, J=7.6 Hz, 3H), 1.21 (d, J=6.4 Hz, 3H), 1.51 (m, 2H), 3.09~3.14 (m, 2H), 3.28 (d, J=4.4 Hz, 1H), 4.82 (br s, 1H), 5.03~5.09 (m, 1H), 5.14~5.17 (m, 1H), 7.22~7.55 (m. 4H)

Example 24

Synthesis of 1-(2-chlorophenyl)-(R)-1-hydroxypropyl-(R)-2-N-isopropylcarbamate (24)

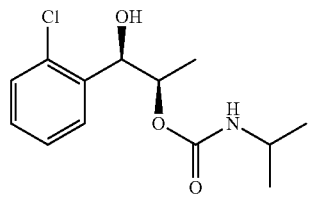 [SMILES: CC(C)NC(=O)O[C@H](C)[C@H](O)c1ccccc1Cl]

The substantially same method as described in Example 22 was conducted, except that isopropylamine was used instead of methylamine solution (CH$_3$NH$_2$ in EtOH), to obtain the title compound (0.16 g, yield 27%).

$^1$H NMR (400 MHz, CDCl$_3$) δ 0.88~1.16 (m, 6H), 1.19~1.26 (m, 3H), 3.34 (s, 1H), 3.71~3.78 (m, 1H), 4.62 (br s, 1H), 5.03 (t, J=5.8 Hz, 1H), 5.13 (d, J=4.9 Hz, 1H), 7.20~7.53 (m, 4H)

Example 25

Synthesis of 1-(2-chlorophenyl)-(R)-1-hydroxypropyl-(R)-2-N-cyclopropylcarbamate (25)

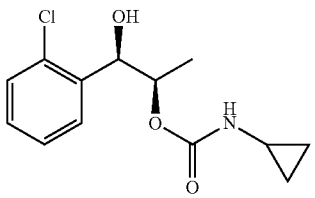 [SMILES: C[C@@H](OC(=O)NC1CC1)[C@H](O)c1ccccc1Cl]

The substantially same method as described in Example 22 was conducted, except that cyclopropylamine was used instead of methylamine solution (CH$_3$NH$_2$ in EtOH), to obtain the title compound (3.7 g, yield 60%).

¹H NMR (400 MHz, CDCl₃) δ0.49~0.54 (m, 2H), 0.74 (d, J=7.2 Hz, 2H), 1.22 (s, 3H), 2.55~2.60 (m, 1H), 3.16 (s, 1H), 5.00 (s, 1H), 5.04~5.11 (m, 1H), 5.16 (s, 1H), 7.23~7.54 (m, 4H)

Example 26

Synthesis of 1-(2-chlorophenyl)-(R)-1-hydroxypropyl-(R)-2-N-cyclohexyl carbamate (26)

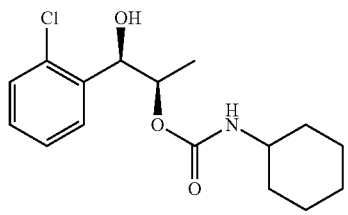 [SMILES: C[C@@H](OC(=O)NC1CCCCC1)[C@H](O)c1ccccc1Cl]

The substantially same method as described in Example 22 was conducted, except that cyclohexylamine was used instead of methylamine solution (CH₃NH₂ in EtOH), to obtain the title compound (1.9 g, yield 28%).

¹H NMR (400 MHz, CDCl₃) δ105~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2 Hz, 1H), 7.20~7.54 (m, 4H)

Example 27

Synthesis of 1-(2-chlorophenyl)-(R)-1-hydroxypropyl-(R)-2-N-benzylcarbamate (27)

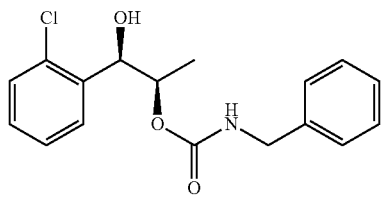 [SMILES: C[C@@H](OC(=O)NCc1ccccc1)[C@H](O)c1ccccc1Cl]

The substantially same method as described in Example 22 was conducted, except that benzylamine was used instead of methylamine solution (CH₃NH₂ in EtOH), to obtain the title compound (0.52 g, yield 19%).

¹H NMR (400 MHz, CDCl₃) δ1.25 (d, J=6 Hz, 3H), 1.64 (s, 1H), 3.13 (d, J=4.4 Hz, 1H), 4.37 (d, J=5.6 Hz, 2H), 5.12~5.19 (m, 2H), 7.23~7.55 (m, 9H)

Example 28

Synthesis of 1-(2-chlorophenyl)-(R)-1-hydroxypropyl-(R)-2-N-bicyclo[2,2,1]heptanecarbamate (28)

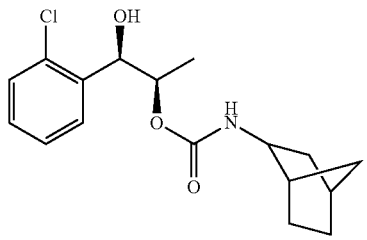 [SMILES: C[C@@H](OC(=O)NC1CC2CCC1C2)[C@H](O)c1ccccc1Cl]

The substantially same method as described in Example 22 was conducted, except that 2-aminonorbornane was used instead of methylamine solution (CH₃NH₂ in EtOH), to obtain the title compound (1.7 g, yield 20~50%).

¹H NMR (400 MHz, CDCl₃) δ108~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 29

Synthesis of 1-(2-chlorophenyl)-1-hydroxypropyl-2-N-methylcarbamate (29)

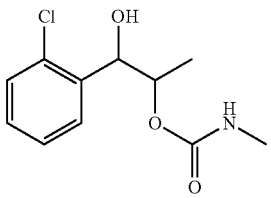 [SMILES: CNC(=O)OC(C)C(O)c1ccccc1Cl]

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

¹H NMR (400 MHz, CDCl₃) δ 1.21 (d, J=6 Hz, 3H), 2.81 (d, J=5 Hz, 3H), 3.14 (d, J=4 Hz, 1H), 4.72 (br s, 1H), 5.07 (dd, J=6 Hz, 1H), 5.16 (t, J=6 Hz, 1H), 7.22~7.56 (m, 4H)

Example 30

Synthesis of 1-(2-chlorophenyl)-1-hydroxypropyl-2-N-propylcarbamate (30)

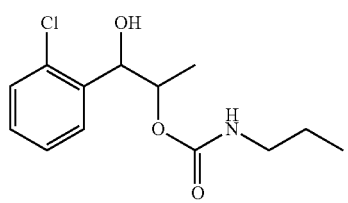 [SMILES: CCCNC(=O)OC(C)C(O)c1ccccc1Cl]

The substantially same method as described in Example 29 was conducted, except that propylamine was used instead of methylamine solution (CH₃NH₂ in EtOH), to obtain the title compound (1.0 g, yield 17%).

¹H NMR (400 MHz, CDCl₃) δ 0.92 (t, J=7 Hz, 3H), 1.21 (d, J=6 Hz, 3H), 1.53 (dd, J=7 Hz, 2H), 3.13 (dd, J=7 Hz, 2H), 3.28 (d, 1H), 4.82 (S, 1H), 5.06 (dd, J=7 Hz, 1H), 5.16 (t, J=5 Hz, 1H), 7.21~7.56 (m, 4H)

Example 31

Synthesis of 1-(2-chlorophenyl)-1-hydroxypropyl-2-N-isopropylcarbamate (31)

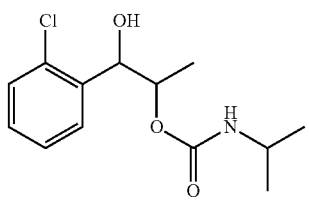 [SMILES: CC(C)NC(=O)OC(C)C(O)c1ccccc1Cl]

The substantially same method as described in Example 29 was conducted, except that isopropylamine was used instead of methylamine solution (CH₃NH₂ in EtOH), to obtain the title compound (0.54 g, yield 16%).

¹H NMR (400 MHz, CDCl₃) δ 1.16 (dd, J=6 Hz, 6H), 1.21 (d, J=6 Hz, 3H), 3.23 (d, J=6 Hz, 1H), 3.75~3.84 (m, 1H), 4.61 (br s, 1H), 5.06 (t, J=6 Hz, 1H), 5.16 (t, J=6 Hz, 1H), 7.22~7.56 (m, 4H)

Example 32

Synthesis of 1-(2-chlorophenyl)-1-hydroxypropyl-2-N-cyclopropylcarbamate (32)

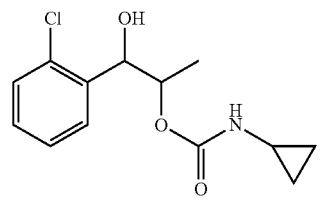 [SMILES: CC(OC(=O)NC1CC1)C(O)c1ccccc1Cl]

The substantially same method as described in Example 29 was conducted, except that cyclopropylamine was used instead of methylamine solution (CH₃NH₂ in EtOH), to obtain the title compound (1.0 g, yield 17%).

¹H NMR (400 MHz, CDCl₃) δ 0.50 (t, J=6 Hz, 2H), 0.77 (t, J=3 Hz, 2H), 1.12 (d, J=7 Hz, 3H), 2.53~2.59 (m, 1H), 3.22 (d, J=4 Hz, 1H), 5.08 (dd, J=6 Hz, 1H), 5.15 (S, 1H), 7.22~7.55 (m, 4H)

Example 33

Synthesis of 1-(2-chlorophenyl)-1-hydroxypropyl-2-N-cyclohexylcarbamate (33)

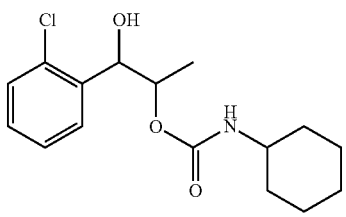 [SMILES: CC(OC(=O)NC1CCCCC1)C(O)c1ccccc1Cl]

The substantially same method as described in Example 29 was conducted, except that cyclohexylamine was used instead of methylamine solution (CH₃NH₂ in EtOH), to obtain the title compound (2.2 g, yield 33%).

¹H NMR (400 MHz, CDCl₃) δ 1.07~1.17 (m, 3H), 1.21 (d, J=6 Hz, 3H), 1.29~1.42 (m, 3H), 1.72 (dd, J=6 Hz, 2H), 1.92

(dd, J=6 Hz, 2H), 3.26 (d, J=4 Hz, 1H), 3.46 (t, J=4 Hz, 1H), 4.68 (d, J=6 Hz, 1H), 5.07 (dd, J=6 Hz, 1H), 5.16 (t, J=6 Hz, 1H), 7.22~7.55 (m, 4H)

Example 34

Synthesis of 1-(2-chlorophenyl)-1-hydroxypropyl-2-N-benzylcarbamate (34)

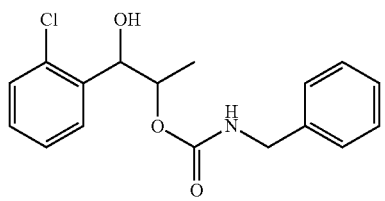

The substantially same method as described in Example 29 was conducted, except that benzylamine was used instead of methylamine solution (CH$_3$NH$_2$ in EtOH), to obtain the title compound (1.3 g, yield 19%).

$^1$H NMR (400 MHz, CDCl$_3$) δ 1.25 (d, J=6 Hz, 3H), 3.16 (d, J=4 Hz, 1H), 4.36 (d, J=6 Hz, 2H), 5.14 (dd, J=6 Hz, 3H), 7.23~7.56 (m, 9H), yield: 19% (1.3 g)

Example 35

Synthesis of 1-(2-chlorophenyl)-1-hydroxypropyl-2-N-bicyclo[2,2,1]heptanecarbamate (35)

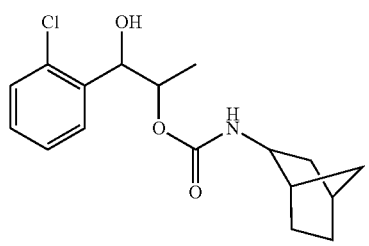 [SMILES: CC(OC(=O)NC1CC2CCC1C2)C(O)c1ccccc1Cl]

The substantially same method as described in Example 29 was conducted, except that 2-aminonorbornane was used instead of methylamine solution (CH$_3$NH$_2$ in EtOH), to obtain the title compound (1.7 g, yield 20~50%).

$^1$H NMR (400 MHz, CDCl$_3$) δ108~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 36

Synthesis of 1-(2,4-dichlorophenyl)-(S)-1-hydroxypropyl-(S)-2-carbamate (36)

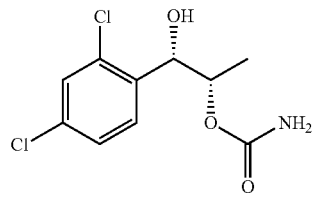

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethylsilanyloxy)propane (Preparation example 69) to obtain the title compound (1.8 g, yield 60~90%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 37

Synthesis of 1-(2,6-dichlorophenyl)-(S)-1-hydroxypropyl-(S)-2-carbamate (37)

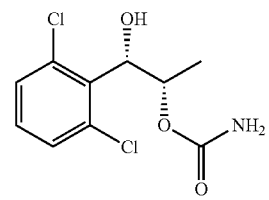 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy)propane (Preparation example 69) to obtain the title compound (2.6 g, yield 60~90%)

Example 38

Synthesis of 1-(2,3-dichlorophenyl)-(S)-1-hydroxypropyl-(S)-2-carbamate (38)

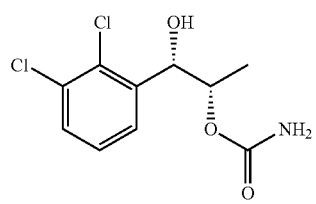

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy)propane (Preparation example 69) to obtain the title compound (1.4 g, yield 60~90%)

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 39

Synthesis of 1-(2,4-dichlorophenyl)-(S)-1-hydroxy-butyl-(S)-2-carbamate (39)

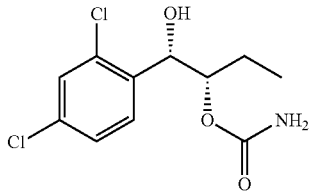 [SMILES: CC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 40

Synthesis of 1-(2,6-dichlorophenyl)-(S)-1-hydroxy-butyl-(S)-2-carbamate (40)

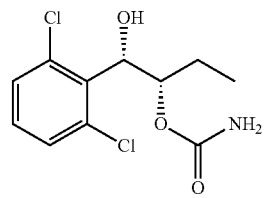 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 41

Synthesis of 1-(2,4-dichlorophenyl)-(S)-1-hydroxy-3-methyl-butyl-(S)-2-carbamate (41)

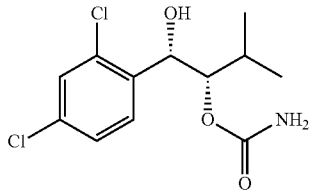

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR (400 MHz, CDCl$_3$) δ1.00 (1, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 42

Synthesis of 1-(2,6-dichlorophenyl)-(S)-1-hydroxy-3-methyl-butyl-(S)-2-carbamate (42)

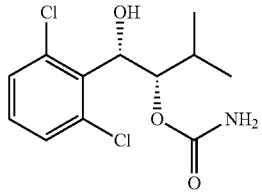 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy)propane (Preparation example 69) to obtain the title compound (2.4 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 43

Synthesis of 1-(2,4-dichlorophenyl)-(S)-1-hydroxy-hexyl-(S)-2-carbamate (43)

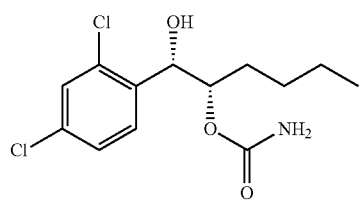 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy)propane (Preparation example 69) to obtain the title compound (2.2 g, yield 60~90%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m 3H)

Example 44

Synthesis of 1-(2,6-dichlorophenyl)-(S)-1-hydroxy-hexyl-(S)-2-carbamate (44)

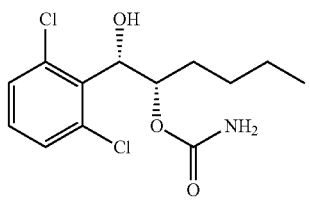 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy)propane (Preparation example 69) to obtain the title compound (2.1 g, yield 60~90%)

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 45

Synthesis of 1-(2,4-dichlorophenyl)-(R)-1-hydroxypropyl-(R)-2-carbamate (45)

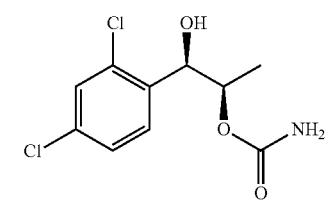 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy)propane (Preparation example 69) to obtain the title compound (1.2 g, yield 60~90%), ¹H NMR (400 MHz, CDCl₃) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 46

Synthesis of 1-(2,6-dichlorophenyl)-(R)-1-hydroxypropyl-(R)-2-carbamate (46)

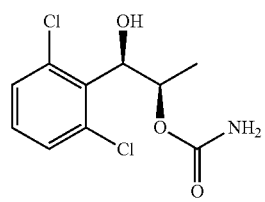 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy)propane (Preparation example 69) to obtain the title compound (1.7 g, yield 60~90%), ¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H), Example 47

Synthesis of 1-(2,3-dichlorophenyl)-(R)-1-hydroxypropyl-(R)-2-carbamate (47)

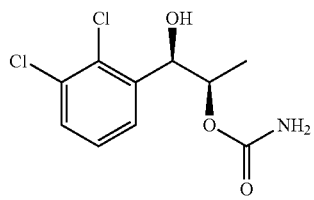 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy)propane (Preparation example 69) to obtain the title compound (2.0 g, yield 60~90%)

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 48

Synthesis of 1-(2,4-dichlorophenyl)-(R)-1-hydroxybutyl-(R)-2-carbamate (48)

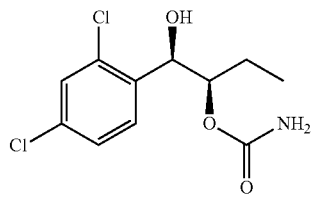 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy)propane (Preparation example 69) to obtain the title compound (2.3 g, yield 60~90%).

¹H NMR (400 MHz, CDCl₃) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 49

Synthesis of 1-(2,6-dichlorophenyl)-(R)-1-hydroxybutyl-(R)-2-carbamate (49)

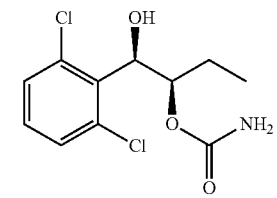 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy)propane (Preparation example 69) to obtain the title compound (2.5 g, yield 60~90%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 50

Synthesis of 1-(2,4-dichlorophenyl)-(R)-1-hydroxy-3-methyl-butyl-(R)-2-carbamate (50)

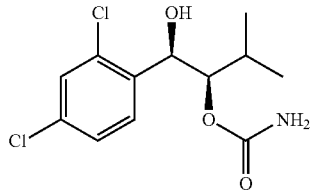 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy)propane (Preparation example 69) to obtain the title compound (2.8 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 51

Synthesis of 1-(2,6-dichlorophenyl)-(R)-1-hydroxy-3-methyl-butyl-(R)-2-carbamate (51)

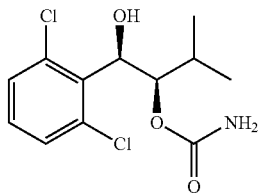 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy)propane (Preparation example 69) to obtain the title compound (2.6 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 52

Synthesis of 1-(2,4-dichlorophenyl)-(R)-1-hydroxy-hexyl-(R)-2-carbamate (52)

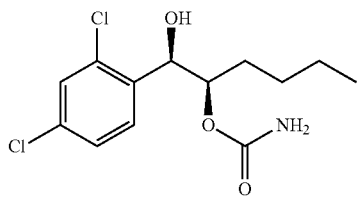 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy)propane (Preparation example 69) to obtain the title compound (2.5 g, yield 60~90%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 53

Synthesis of 1-(2,6-dichlorophenyl)-(R)-1-hydroxy-hexyl-(R)-2-carbamate (53)

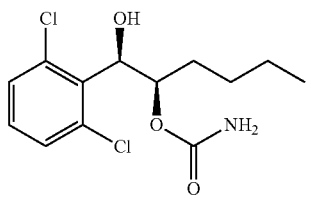 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy)propane (Preparation example 69) to obtain the title compound (2.4 g, yield 60~90%).

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 54

Synthesis of 1-(2,4-dichlorophenyl)-1-hydroxypropyl-2-carbamate (54)

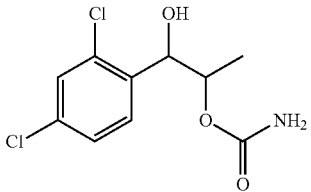 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 55

Synthesis of 1-(2,6-dichlorophenyl)-1-hydroxypropyl-2-carbamate (55)

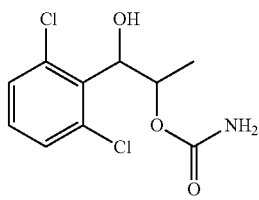 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 56

Synthesis of 1-(2,3-dichlorophenyl)-1-hydroxypropyl-2-carbamate (56)

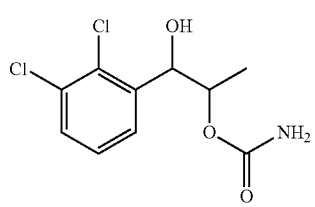 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy)propane (Preparation example 69) to obtain the title compound (1.6 g, yield 60~90%).

Example 57

Synthesis of 1-(2,4-dichlorophenyl)-1-hydroxybutyl-2-carbamate (57)

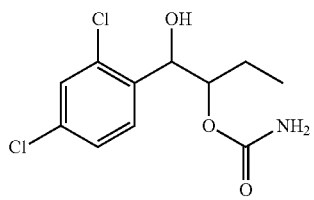 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 58

Synthesis of 1-(2,6-dichlorophenyl)-1-hydroxybutyl-2-carbamate (58)

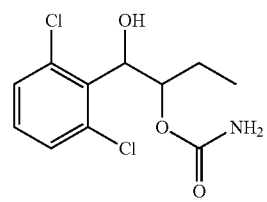 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy)propane (Preparation example 69) to obtain the title compound (2.4 g, yield 60~90%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 59

Synthesis of 1-(2,4-dichlorophenyl)-1-hydroxy-3-methyl-butyl-2-carbamate (59)

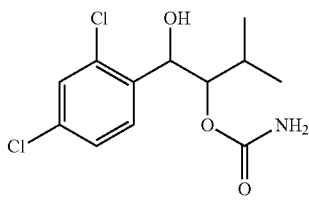 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy)propane (Preparation example 69) to obtain the title compound (1.9 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 60

Synthesis of 1-(2,6-dichlorophenyl)-1-hydroxy-3-methyl-butyl-2-carbamate (60)

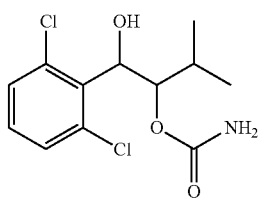 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy)propane (Preparation example 69) to obtain the title compound (1.7 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 61

Synthesis of 1-(2,4-dichlorophenyl)-1-hydroxyhexyl-2-carbamate (61)

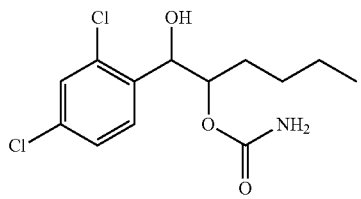 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy)propane (Preparation example 69) to obtain the title compound (2.6 g, yield 60~90%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 62

Synthesis of 1-(2,6-dichlorophenyl)-1-hydroxyhexyl-2-carbamate (62)

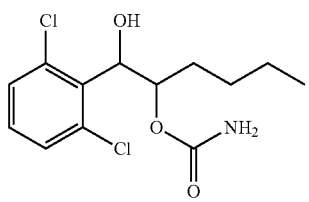 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy)propane (Preparation example 69) to obtain the title compound (2.5 g, yield 60~90%).

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 63

Synthesis of 1-(2-fluorophenyl)-(S)-1-hydroxypropyl-(S)-2-carbamate (63)

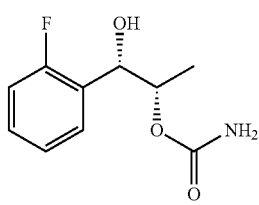

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy) propane (Preparation example 69) to obtain the title compound (1.8 g, yield 60~90%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 64

Synthesis of 1-(2-fluorophenyl)-(R)-1-hydroxypropyl-(R)-2-carbamate (64)

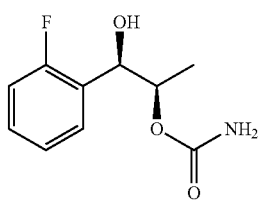

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 65

Synthesis of 1-(2-iodophenyl)-(S)-1-hydroxypropyl-(S)-2-carbamate (65)

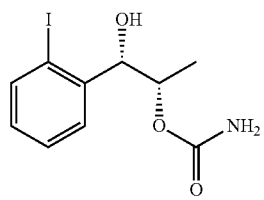

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Example 66

Synthesis of 1-(2-iodophenyl)-(R)-1-hydroxypropyl-(R)-2-carbamate (66)

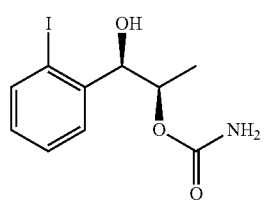

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy)propane (Preparation example 69) to obtain the title compound (1.7 g, yield 60~90%).

¹H NMR (400 MHz, CDCl₃) δ1.27 (d, J=6.4 Hz, 3H), 2.95 (d, J=3.6 Hz, 1H), 4.73 (br s, 2H), 5.01~5.11 (m, 2H), 7.01~7.86 (m, 4H)

Example 67

Synthesis of 1-(2-iodophenyl)-(S)-1-hydroxybutyl-(S)-2-carbamate (67)

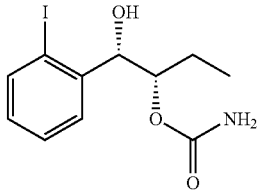 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy)propane (Preparation example 69) to obtain the title compound (2.1 g, yield 60~90%).

¹H NMR (400 MHz, CDCl₃) δ1.27 (d, J=6.4 Hz, 3H), 3.09 (br s, 1H), 4.83 (br s, 2H), 5.00~5.10 (m, 2H), 7.00~7.76 (m, 4H)

Example 68

Synthesis of 1-(2-chlorophenyl)-(S)-2-hydroxypropyl-(S)-1-carbamate (68)

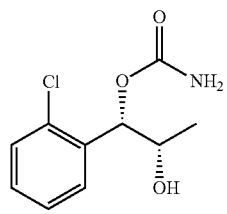

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH₄OH, 4 ml) was added thereto. When the reaction was completed, the obtained product was washed with 1M HCl solution and ethylacetate (EA). The separated organic layer was dehydrated with anhydrous magnesium sulfate (MgSO₄), filtrated, and concented under reduced pressure. The concentrated residue was purified by a silica gel column chromatography, to obtain the title compound (0.28 g, yield 10~30%).

¹H NMR (400 MHz, CDCl₃) δ1.24 (d, J=6.8 Hz, 3H), 2.13 (d, J=4.4 Hz, 1H), 4.12~4.16 (m, 1H), 4.85 (br s, 2H), 5.98 (d, J=5.6 Hz, 1H), 7.24~7.43 (m, 4H)

Example 69

Synthesis of 1-(2-chlorophenyl)-(R)-2-hydroxypropyl-(R)-1-carbamate (69)

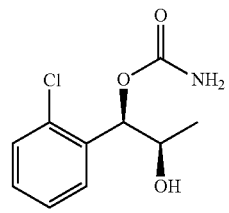

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

¹H NMR (400 MHz, CDCl₃) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Example 70

Synthesis of 1-(2-chlorophenyl)-2-hydroxypropyl-1-carbamate (70)

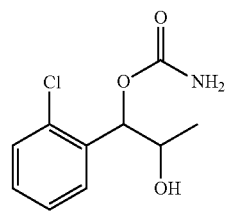

The substantially same method as described in Example 68 was conducted, except that 1-(2-chlorophenyl)-(R,R)-1,2-propanediol (Preparation Example 16) was used instead of 1-(2-chlorophenyl)-(S,S)-1,2-propanediol (Preparation example 14) to obtain the title compound (0.16 g, yield 10~30%).

¹H NMR (400 MHz, CDCl₃) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Example 71

Synthesis of 1-(2-chlorophenyl)-(S)-2-hydroxypropyl-(S)-1-N-methylcarbamate (71)

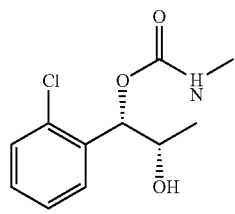 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

¹H NMR (400 MHz, CDCl₃) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Example 72

Synthesis of 1-(2-chlorophenyl)-(R)-2-hydroxypropyl-(R)-1-N-methylcarbamate (72)

A regioisomer of monocarbamate was separated and purified by conducting the silica gel column chromatography as described in Example 22, to obtain the title compound (0.69 g, yield 10~30%).

¹H NMR (400 MHz, CDCl₃) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Example 73

Synthesis of 1-(2-chlorophenyl)-2-hydroxypropyl-1-N-methylcarbamate (73)

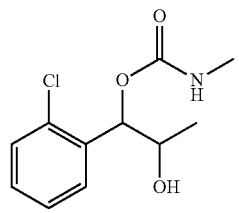 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

¹H NMR (400 MHz, CDCl₃) δ 1.22 (d, J=6 Hz, 3H), 2.15 (d, J=4 Hz, 1H), 2.81 (d, J=5 Hz, 3H), 4.12 (dd, J=6 Hz, 1H), 4.83 (br s, 1H), 6.00 (d, J=6 Hz, 1H), 7.23~7.41 (m, 4H)

Example 74

Synthesis of 1-(2-chlorophenyl)-(S)-2-hydroxypropyl-(S)-1-N-propylcarbamate (74)

A regioisomer of monocarbamate was separated and purified by conducting the silica gel column chromatography as described in Example 16, to obtain the title compound (0.15 g, yield 10~30%).

¹H NMR (400 MHz, CDCl₃) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 75

Synthesis of 1-(2-chlorophenyl)-(R)-2-hydroxypropyl-(R)-1-N-propylcarbamate (75)

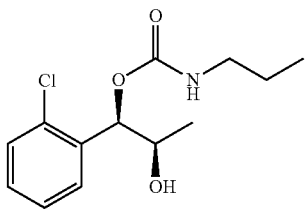 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 76

Synthesis of 1-(2-chlorophenyl)-2-hydroxypropyl-1-N-propylcarbamate (76)

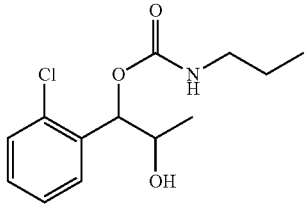 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 77

Synthesis of 1-(2-chlorophenyl)-(S)-2-hydroxypropyl-(S)-1-N-isopropylcarbamate (77)

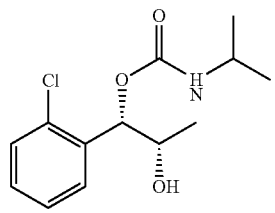 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).

$^1$H NMR (400 MHz, CDCl$_3$) δ1.10 (d, J=6.0 Hz, 3H), 1.15~1.19 (m, 6H), 2.41 (s, 1H), 3.76~4.08 (m, 1H), 4.34 (s, 1H), 4.83 (br s 1H), 5.95 (d, J=5.3 Hz, 1H), 7.19~7.39 (m, 4H)

Example 78

Synthesis of 1-(2-chlorophenyl)-(R)-2-hydroxypropyl-(R)-1-N-isopropylcarbamate (78)

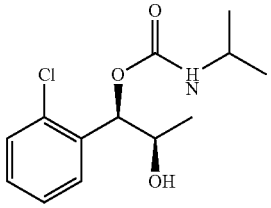 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).

¹H NMR (400 MHz, CDCl₃) δ1.13 (d, J=6 Hz, 3H), 1.20 (dd, J=9.2 Hz, 6H), 2.23 (s, 1H), 3.77~3.82 (m, 1H), 4.10 (s, 1H), 4.76 (br s, 1H), 5.98 (d, J=5.6 Hz, 1H), 7.23~7.41 (m, 4H)

Example 79

Synthesis of 1-(2-chlorophenyl)-2-hydroxypropyl-1-N-isopropylcarbamate (79)

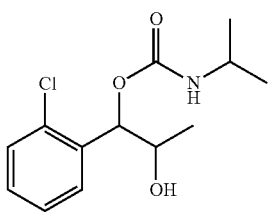 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 10~30%).

¹H NMR (400 MHz, CDCl₃) δ 1.14 (d, J=6 Hz, 3H), 1.21 (dd, J=6 Hz, 6H), 2.16 (d, J=5 Hz, 1H), 3.81 (t, J=6 Hz, 1H), 4.11 (d, J=5 Hz, 1H), 4.73 (br s, 1H), 5.98 (d, J=5 Hz, 1H), 7.24~741 (m, 4H)

Example 80

Synthesis of 1-(2-chlorophenyl)-(S)-2-hydroxypropyl-(S)-1-N-cyclopropylcarbamate (80)

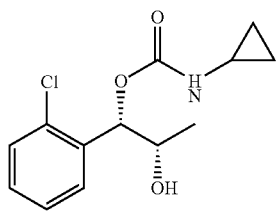 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

¹H NMR (400 MHz, CDCl₃) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Example 81

Synthesis of 1-(2-chlorophenyl)-(R)-2-hydroxypropyl-(R)-1-N-cyclopropylcarbamate (81)

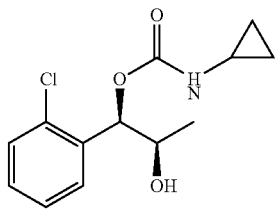 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

¹H NMR (400 MHz, CDCl₃) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Example 82

Synthesis of 1-(2-chlorophenyl)-2-hydroxypropyl-1-N-cyclopropylcarbamate (82)

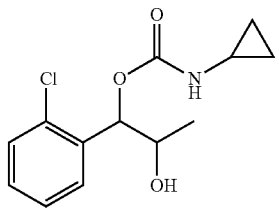 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

¹H NMR (400 MHz, CDCl₃) δ 0.71 (s, 2H), 1.19 (d, J=6 Hz, 3H), 2.45 (S, 1H), 2.57 (S, 1H), 4.08~4.12 (m, 1H), 5.26 (s, 1H), 5.97 (d, J=4 Hz, 1H), 7.22~7.54 (m, 4H)

Example 83

Synthesis of 1-(2-chlorophenyl)-(S)-2-hydroxypropyl-(S)-1-N-cyclohexylcarbamate (83)

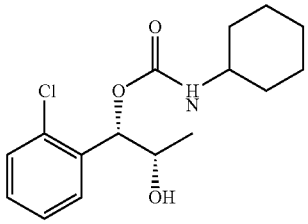 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).
¹H NMR (400 MHz, CDCl₃) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Example 84

Synthesis of 1-(2-chlorophenyl)-(R)-2-hydroxypropyl-(R)-1-N-cyclohexylcarbamate (84)

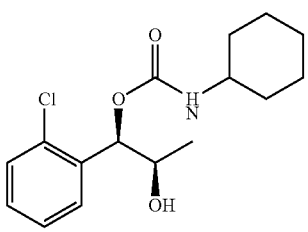 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).
¹H NMR (400 MHz, CDCl₃) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Example 85

Synthesis of 1-(2-chlorophenyl)-2-hydroxypropyl-1-N-cyclohexylcarbamate (85)

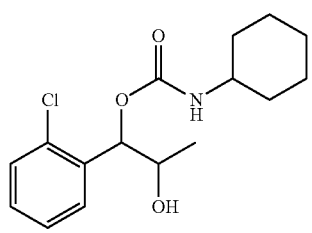 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).
¹H NMR (400 MHz, CDCl₃) δ 1.12~1.19 (m, 3H), 1.22 (d, J=6 Hz, 3H), 1.27~1.37 (m, 1H), 1.71 (t, J=6 Hz, 2H), 1.86~1.88 (m, 1H), 1.97~2.00 (m, 1H), 2.18 (d, J=4 Hz, 1H), 3.47 (S, 1H), 4.12 (t, J=6 Hz, 1H), 4.78 (S, 1H), 5.97 (d, J=6 Hz, 1H), 7.23~7.40 (m, 4H)

Example 86

Synthesis of 1-(2-chlorophenyl)-(S)-2-hydroxypropyl-(S)-1-N-benzylcarbamate (86)

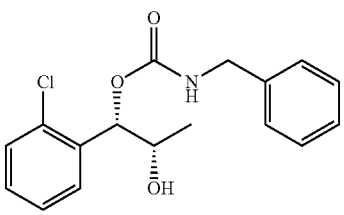

A regioisomer of monocarbamate was separated and purified by conducting the silica gel column chromatography as described in Example 20, to obtain the title compound (0.19 g, yield 10~30%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 87

Synthesis of 1-(2-chlorophenyl)-(R)-2-hydroxypropyl-(R)-1-N-benzylcarbamate (87)

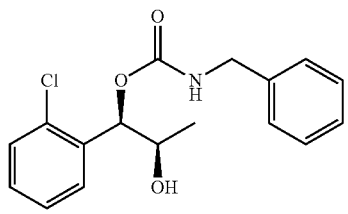 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 88

Synthesis of 1-(2-chlorophenyl)-2-hydroxypropyl-1-N-benzylcarbamate (88)

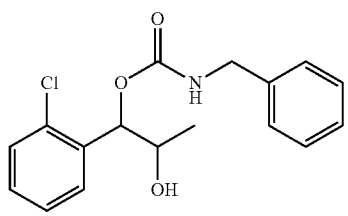 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 89

Synthesis of 1-(2,4-dichlorophenyl)-(S)-2-hydroxypropyl-(S)-1-carbamate (89)

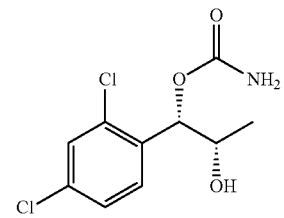

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).

¹H NMR (400 MHz, CDCl₃) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30 (d, J=8.4 Hz, 1H), 7.39 (d, J=2.0 Hz, 2H), 7.50 (dd, J=8.4 Hz, 2.0 Hz, 1H)

Example 90

Synthesis of 1-(2,6-dichlorophenyl)-(S)-2-hydroxypropyl-(S)-1-carbamate (90)

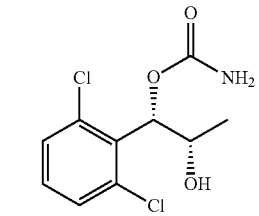 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).

¹H NMR (400 MHz, CDCl₃) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 91

Synthesis of 1-(2,3-dichlorophenyl)-(S)-2-hydroxypropyl-(S)-1-carbamate (91)

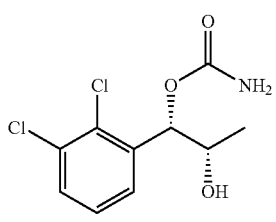

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 92

Synthesis of 1-(2,4-dichlorophenyl)-(S)-2-hydroxybutyl-(S)-1-carbamate (92)

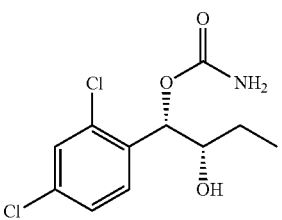 [SMILES: CC[C@H](O)[C@@H](OC(N)=O)c1ccc(Cl)cc1Cl]

The substantially same method as described in Example 68 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14), to obtain the title compound (0.07 g, yield 10~30%).

¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 93

Synthesis of 1-(2,6-dichlorophenyl)-(S)-2-hydroxybutyl-(S)-1-carbamate (93)

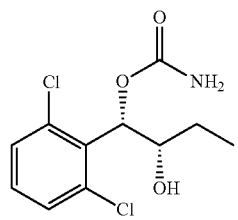 [SMILES: CC[C@H](O)[C@@H](OC(N)=O)c1c(Cl)cccc1Cl]

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 94

Synthesis of 1-(2,4-dichlorophenyl)-(S)-2-hydroxy-3-methyl-butyl-(S)-1-carbamate (94)

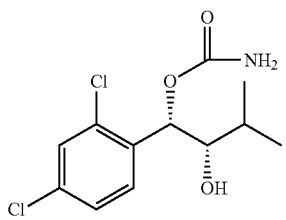

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

¹H NMR (400 MHz, CDCl₃) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 95

Synthesis of 1-(2,6-dichlorophenyl)-(S)-2-hydroxy-3-methyl-butyl-(S)-1-carbamate (95)

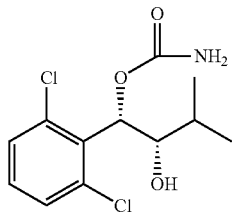

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

¹H NMR (400 MHz, CDCl₃) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 96

Synthesis of 1-(2,4-dichlorophenyl)-(S)-2-hydroxy-hexyl-(S)-1-carbamate (96)

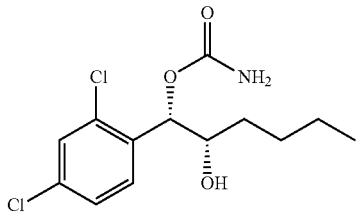 [SMILES: CCCC[C@H](O)[C@@H](OC(N)=O)c1ccc(Cl)cc1Cl]

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

¹H NMR (400 MHz, CDCl₃) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 97

Synthesis of 1-(2,6-dichlorophenyl)-(S)-2-hydroxy-hexyl-(S)-1-carbamate (97)

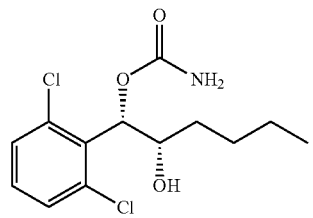 [SMILES: CCCC[C@H](O)[C@@H](OC(N)=O)c1c(Cl)cccc1Cl]

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

¹H NMR (400 MHz, CDCl₃) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Example 98

Synthesis of 1-(2,4-dichlorophenyl)-(R)-2-hydroxypropyl-(R)-1-carbamate (98)

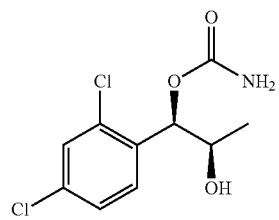 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Example 99

Synthesis of 1-(2,6-dichlorophenyl)-(R)-2-hydroxypropyl-(R)-1-carbamate (99)

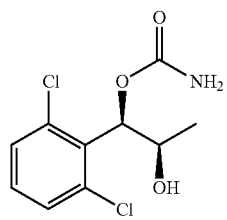 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 100

Synthesis of 1-(2,3-dichlorophenyl)-(R)-2-hydroxypropyl-(R)-1-carbamate (100)

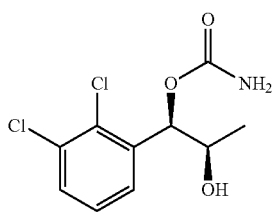 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 101

Synthesis of 1-(2,4-dichlorophenyl)-(R)-2-hydroxybutyl-(R)-1-carbamate (101)

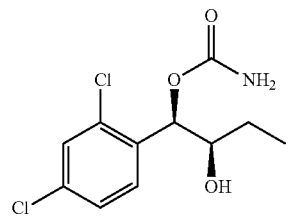 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 102

Synthesis of 1-(2,6-dichlorophenyl)-(R)-2-hydroxybutyl-(R)-1-carbamate (102)

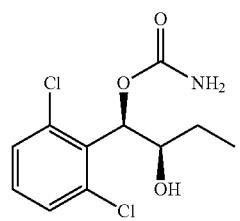 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%). $^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 103

Synthesis of 1-(2,4-dichlorophenyl)-(R)-2-hydroxy-3-methyl-butyl-(R)-1-carbamate (103)

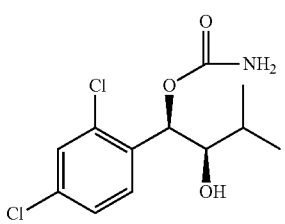 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 104

Synthesis of 1-(2,6-dichlorophenyl)-(R)-2-hydroxy-3-methyl-butyl-(R)-1-carbamate (104)

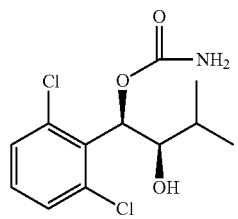 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 105

Synthesis of 1-(2,4-dichlorophenyl)-(R)-2-hydroxy-hexyl-(R)-1-carbamate (105)

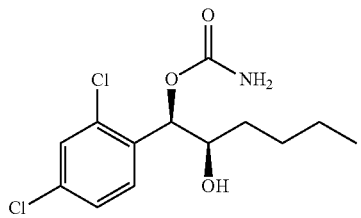 [SMILES: CCCC[C@@H](O)[C@H](OC(N)=O)c1ccc(Cl)cc1Cl]

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 106

Synthesis of 1-(2,6-dichlorophenyl)-(R)-2-hydroxy-hexyl-(R)-1-carbamate (106)

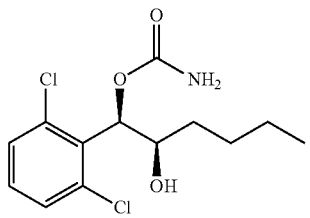 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

¹H NMR (400 MHz, CDCl₃) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Example 107

Synthesis of 1-(2,4-dichlorophenyl)-2-hydroxypropyl-1-carbamate (107)

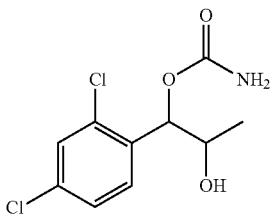 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).
¹H NMR (400 MHz, CDCl₃) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Example 108

Synthesis of 1-(2,6-dichlorophenyl)-2-hydroxypropyl-1-carbamate (108)

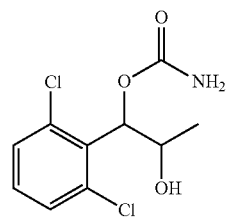 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

¹H NMR (400 MHz, CDCl₃) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 109

Synthesis of 1-(2,3-dichlorophenyl)-(R)-2-hydroxypropyl-(R)-1-carbamate (109)

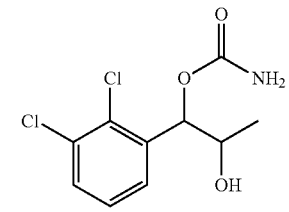 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).
¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 110

Synthesis of 1-(2,4-dichlorophenyl)-2-hydroxybutyl-1-carbamate (110)

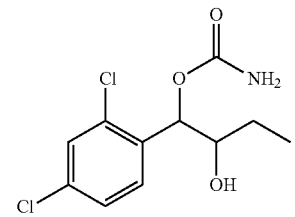 [SMILES: CCC(O)C(OC(N)=O)c1ccc(Cl)cc1Cl]

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 111

Synthesis of 1-(2,6-dichlorophenyl)-2-hydroxybutyl-1-carbamate (111)

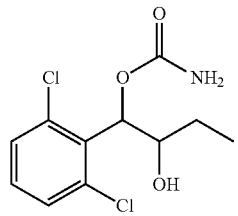 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 112

Synthesis of 1-(2,4-dichlorophenyl)-2-hydroxy-3-methyl-butyl-1-carbamate (112)

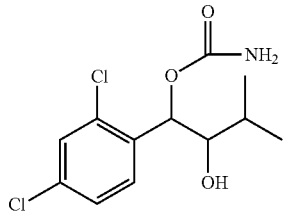 [SMILES: CC(C)C(O)C(OC(N)=O)c1ccc(Cl)cc1Cl]

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

¹H NMR (400 MHz, CDCl₃) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 113

Synthesis of 1-(2,6-dichlorophenyl)-2-hydroxy-3-methyl-butyl-1-carbamate (113)

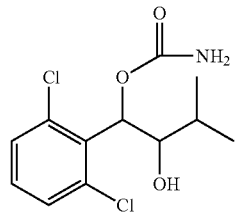 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

¹H NMR (400 MHz, CDCl₃) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 114

Synthesis of 1-(2,4-dichlorophenyl)-2-hydroxyhexyl-1-carbamate (114)

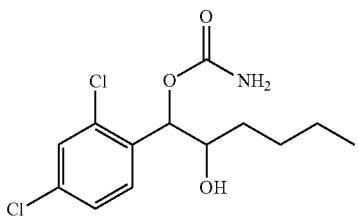

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 115

Synthesis of 1-(2,6-dichlorophenyl)-2-hydroxyhexyl-1-carbamate (115)

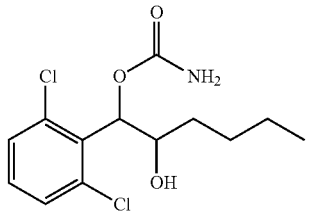

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Compounds 1 to 115 produced in Examples 1 to 115 were summarized in following Tables 1 to 3.

TABLE 1

Compounds 1 to 67 having the structure of Chemical Formula 1 where 'A' is a carbamoyl derivative and 'B' is H

| No. | X | n (position) | 1$^{st}$ Chiral | 2$^{nd}$ Chiral | R$^1$ | A = carbamoyl derivative R$^2$ = | B B = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac. | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac. | Rac. | Me | H | H |
| 55 | Cl | 2(2,6-) | Rac. | Rac. | Me | H | H |
| 56 | Cl | 2(2,3-) | Rac. | Rac. | Me | H | H |
| 57 | Cl | 2(2,4-) | Rac. | Rac. | Et | H | H |
| 58 | Cl | 2(2,6-) | Rac. | Rac. | Et | H | H |
| 59 | Cl | 2(2,4-) | Rac. | Rac. | Isopropyl | H | H |
| 60 | Cl | 2(2,6-) | Rac. | Rac. | Isopropyl | H | H |
| 61 | Cl | 2(2,4-) | Rac. | Rac. | butyl | H | H |
| 62 | Cl | 2(2,6-) | Rac. | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'A' is H and 'B' is a carbamoyl derivative

| No. | X | n (position) | 1$^{st}$ Chiral | 2$^{nd}$ Chiral | R$^1$ | A A = H | B = carbamoyl derivative R$^3$ = |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |

TABLE 2-continued

Compounds 68 to 115 having the structure of Chemical Formula 1 where 'A' is H and 'B' is a carbamoyl derivative

| No. | X | n (position) | $1^{st}$ Chiral | $2^{nd}$ Chiral | $R^1$ | A A = H | B B = carbamoyl derivative $R^3$ = |
|---|---|---|---|---|---|---|---|
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Experimental Example 1

Hot-Plate Test

To examine the pain relief effect of the phenyl carbamate compounds, a hot-plate test was conducted in general pain animal model referring to Current Protocols in Neuroscience; Behavioral Neuroscience Unit 8.9.

ICR mice (male, 30-35 g; Orient Bio, Korea) were habituated before test in test room for 1 hour Animals were fasted 2 hr before administration of compounds. Each of Compound 1, 2, 3, 4, 5, 63, 65, and 67 was orally administered at the dose of 150 mg/kg, 10 ul/g, bw (n=7~10/group). All compounds were dissolved in a vehicle of 30% (v/v) PEG 400 or 20% (v/v) Tween 80. The control group was treated the vehicle without compounds.

0.5 hr after the administration of compounds, the mice were put on a hot plate pre-heated to 55±1° C. (Hu, X. et al, 2008), and then, measured as the withdrawal latency (cut-off time: 30 sec) time until the point when each mouse was taking off a paw from the plate, shaking, licking a paw or hind leg, or jumping from the plate. The relative values compared to the control (% control) were calculated and shown in Table 3 and FIG. 1.

TABLE 3

Effect of compound examples in hot-plate test.

| Example No. | Name of Compounds | Vehicle | Hot-plate test (150 mg/kg, 0.5 h, po) % Control |
|---|---|---|---|
| 1 | 1-(2-chlorophenyl)-(S)-1-hydroxypropyl-(S)-2-carbamate | 30% PEG 400 | 135.7% |
| 2 | 1-(2-chlorophenyl)-(R)-1-hydroxypropyl-(R)-2-carbamate | | 129.8% |
| 3 | 1-(2-chlorophenyl)-1-hydroxypropyl-2-carbamate | | 120.5% |
| 4 | 1-(2-chlorophenyl)-(S)-1-hydroxypropyl-(R)-2-carbamate | | 108.2% |
| 5 | 1-(2-chlorophenyl)-(R)-1-hydroxypropyl-(S)-2-carbamate | | 145.5% |
| 63 | 1-(2-fluorophenyl)-(S)-1-hydroxypropyl-(S)-2-carbamate | | 183.1% |
| 65 | 1-(2-iodophenyl)-(S)-1-hydroxypropyl-(S)-2-carbamate | 20% Tween 80 | 104.1% |
| 67 | 1-(2-iodophenyl)-(S)-1-hydroxybutyl-(S)-2-carbamate | | 131.4% |

Experimental Example 2

Writhing Test

To examine the pain relief effect of the phenyl carbamate compounds, a writhing test was conducted in general pain animal model referring to Fischer, L. G. et al. (2008).

ICR mice (male, 24-28 g; Orient Bio, Korea) were habituated before test in test room for 1 hour Animals were fasted 2 hr, before administration of compounds. Each of Compound 1, 2, 3, 4, 5, 63, 65, and 67 was orally administered at the dose of 20 mg/kg, 10 ul/g, bw (n=3~5/group). All compounds were dissolved in a vehicle of 30% (v/v) PEG 400 or 20% (v/v) Tween 80. The control group was treated the vehicle without compounds.

One hour after the administration of Compounds, 0.6% acetic acid at the dose of 10 ul/g, bw was injected into the mice. Animals were habituated in the cage for 5 min 5 min after habituation, the number of writhes (abdominal constriction) for 15 min was counted referring to Korzeniewska-Rybicka, I. et al. (1998) and compared with that of a control.

Figure 2:
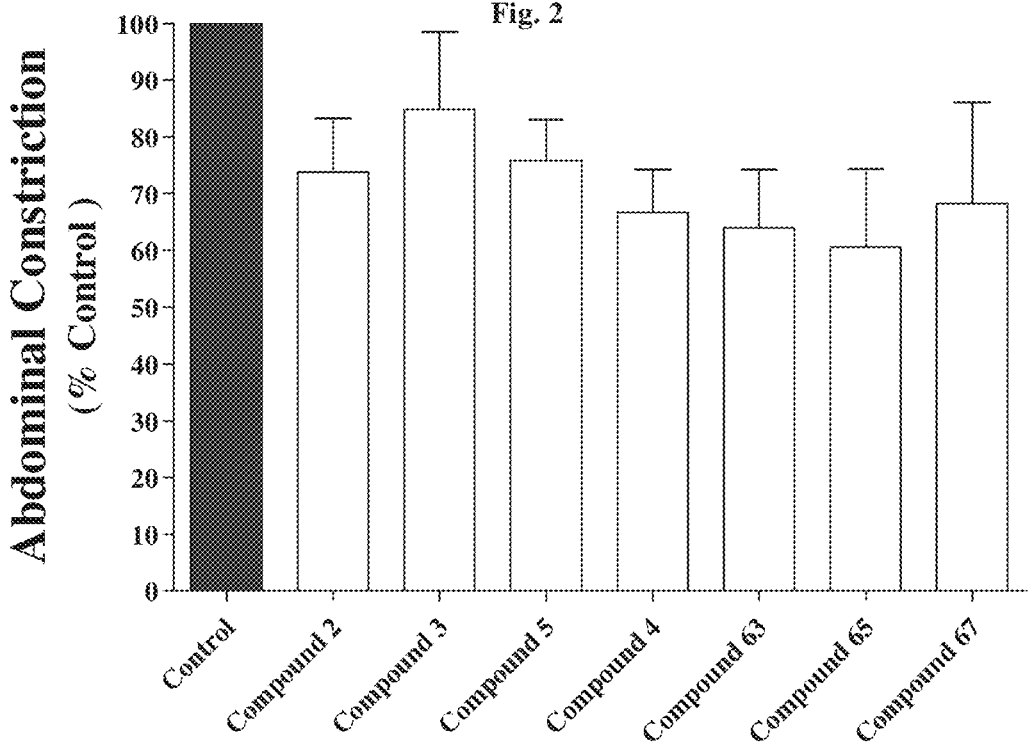
FIG. 2 is a graph showing withdrawal latency measured by writhing test for various phenyl carbamate compounds, wherein the value (% control) are expressed as the mean±S.E.M. (n=3~5), and statistic analysis was performed by One-way ANOVA at 1 hr: $F(7.24)=1.512$, $p<0.05$ (Turkey's test).

The relative values compared to the control (% control) were calculated and shown in Table 4 and FIG. 2.

TABLE 4

Effect of compound examples in writhing test.

| Example No. | Name of Compounds | Vehicle | Writhing test (20 mg/kg, 1 h, po) % Control |
|---|---|---|---|
| 1 | 1-(2-chlorophenyl)-(S)-1-hydroxypropyl-(S)-2-carbamate | 30% PEG 400 | ED50: 14.1 mg/kg |
| 2 | 1-(2-chlorophenyl)-(R)-1-hydroxypropyl-(R)-2-carbamate | | 73.8% |

TABLE 4-continued

Effect of compound examples in writhing test.

| Example No. | Name of Compounds | Vehicle | Writhing test (20 mg/kg, 1 h, po) % Control |
|---|---|---|---|
| 3 | 1-(2-chlorophenyl)-1-hydroxypropyl-2-carbamate | | 84.8% |
| 4 | 1-(2-chlorophenyl)-(S)-1-hydroxypropyl-(R)-2-carbamate | | 75.5% |
| 5 | 1-(2-chlorophenyl)-(R)-1-hydroxypropyl-(S)-2-carbamate | | 66.6% |
| 63 | 1-(2-fluorophenyl)-(S)-1-hydroxypropyl-(S)-2-carbamate | | 63.9% |
| 65 | 1-(2-iodophenyl)-(S)-1-hydroxypropyl-(S)-2-carbamate | 20% Tween 80 | 60.6% |
| 67 | 1-(2-iodophenyl)-(S)-1-hydroxybutyl-(S)-2-carbamate | | 68.3% |

Experimental Example 3

Evaluation of Antiallodynic Activity on Chung Model

Male Sprague-Dawley rats (200-220 g, Orient Bio, Korea) were habituated for 1 week before the experiment and allowed free access to food and water throughout the experimentation. Room temperature and humidity were maintained at 24±2° C. and 50±10%, respectively. Neuropathic surgery (SNL, Spinal nerve ligation) model was done as described in Kim and Chung (1992). Briefly, animal under gaseous anesthesia with isoflurane a 4:4 flow ratio of $NO_2$. The left lumber spinal nerve L5 and L6 were isolated and tightly ligated with 4~0 silk thread. The wound was treated with a gentamicin antibiotics solution (4 mg/kg, 4 ul/g, bw), and the wound muscle was closed with cat cut chrome 4/0 thread and skin was closed dafilon 4/0 tread. Sham controls were prepared in the same manner as the spinal nerves were exposed, but no ligated L5 and L6 nerves. But, vehicle controls were identical to SNL model, except for administration of vehicles.

Tactile sensitivity (Mechanical allodynia) was evaluated using von Frey monofilaments before and after treatment and animals were used withdrawal threshold value was less than 4 g. One week after surgery, SNL-operated animals (n=4~6), sham-operated animals (n=4~10) and SNL animals (n=4~13) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

All animals were fasted 18 h before the administration of the compounds. Antiallodynic effect of compounds of Examples 1, 63 and 65 were evaluated at the dose of 5, 10 and 30 mg/kg (n=5~6), orally administrated in a volume of 5 ul/g, bw in a vehicle of 30% (v/v) PEG 400 (Examples 1 and 63) or 20% (v/v) Tween 80 (Example 65). The test was performed at the peak time of efficacy (1 hr) after compound administration.

Figure 3:
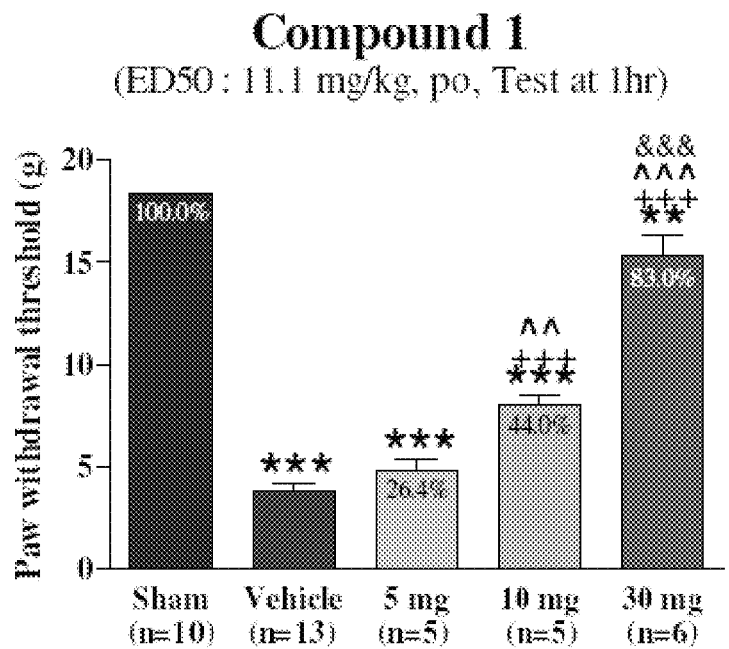
FIG. 3 is a graph showing paw withdrawal threshold measured by using the von Frey monofilament for Compound 1 (on SNL model), wherein the values (% control) are expressed as the mean±S.E.M. (n=5~13), and statistical analysis was used by One-way ANOVA at 1 hr: $F(4.34)=199.4$, $p<0.0001$ (Tukey's test) *; vs Sham, $p<0.001$, ; vs Sham, $p<0.01$, +++; vs Vehicle, $p<0.001$, ^^^; vs 5 mg, $p<0.001$, ^^; vs 5 mg, $p<0.01$, &&&; vs 10 mg, $p<0.001$.
Figure 4:
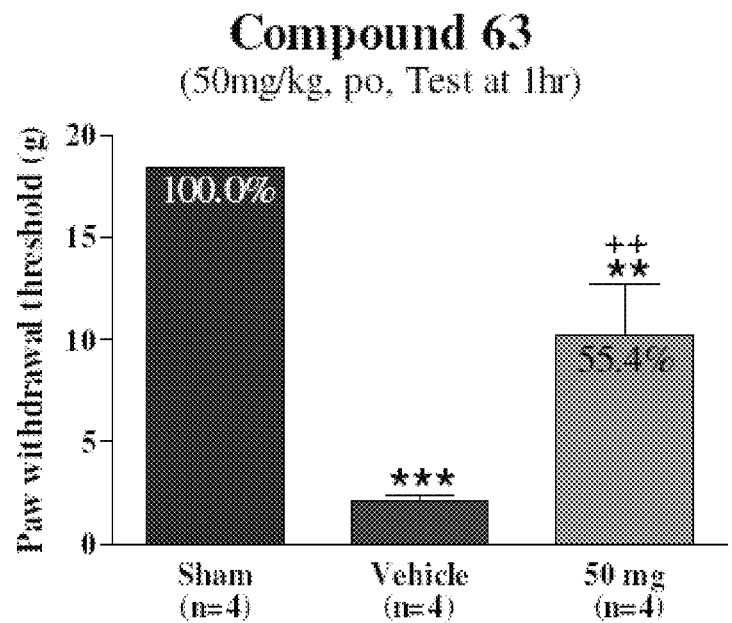
FIG. 4 is a graph showing paw withdrawal threshold measured by using the von Frey monofilament for Compound 63 (on SNL model), wherein the values (% control) are expressed as the mean±S.E.M. (n=4) and statistical analysis was used by One-way ANOVA at 1 hr: $F(2.9)=31.76$, $p<0.001$ (Tukey's test) *; vs Sham, $p<0.001$, ; vs Sham, $p<0.01$, ++; vs Vehicle, $p<0.01$.
Figure 5:
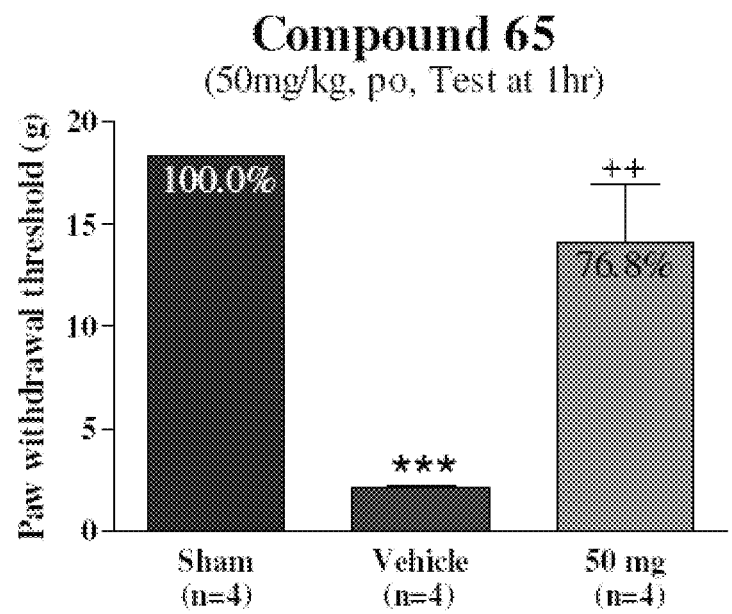
FIG. 5 is a graph showing paw withdrawal threshold measured by using the von Frey monofilament for Compound 65 (on SNL model), wherein the values (% control) are expressed as the mean±S.E.M. (n=4) and statistical analysis was used by One-way ANOVA at 1 hr: $F(2.9)=25.84$, $p<0.001$ (Tukey's test) ***; vs Sham, $p<0.001$, ++; vs Vehicle, $p<0.01$.

The relative values compared to the sham group (% control) were calculated and shown in Table 5 and FIGS. 3-5, which show an antiallodynic effect of the test compounds on SNL model in rats.

TABLE 5

Antiallodynic effect of compound examples on SNL model

| Example No. | Name of Compounds | Vehicle | SNL (50 mg/kg, 1 h, p.o.) % Control |
|---|---|---|---|
| 1 | 1-(2-chlorophenyl)-(S)-1-hydroxypropyl-(S)-2-carbamate (SS) | 30% PEG 400 | ED50: 11.1 mg/kg |
| 63 | 1-(2-fluorophenyl)-(S)-1-hydroxypropyl-(S)-2-carbamate (SS) | | 55.4% |
| 65 | 1-(2-iodophenyl)-(S)-1-hydroxypropyl-(S)-2-carbamate (SS) | 20% Tween 80 | 76.8% |

Experimental Example 4

Evaluation of Antiallodynic Activity on Vincristine-Induced Pain Model

Male, Sprague-Dawley rats (300-320 g, Nara Bio, Korea) were habituated for 1 week before surgery and allowed free access to food and water throughout the experimentation. Room temperature and humidity were maintained at 24±2° C. and 50±10%, respectively.

Vincristine was established by the procedure of Natsuko et al. (2001) with minor modifications. Vincristine was intravenously infused continuously for 14 days using a mini-osmotic pump as follows. Vincristine sulfate solution (Hospira, Australia) was diluted with 0.9% saline to 30 ug/kg, final dose. The pumps (Alzet Model 2002, USA) were filled with the vincristine solution and primed by incubation at 37° C. for 4 h before the infusion. Briefly, animal under gaseous anesthesia with isoflurane a 4:4 flow ratio of $NO_2$. Catheter made from PE-60 tube was inserted into an external jugular vein in rat Sham controls were prepared in the same manner as expose of the external jugular vein, but, not cut down of external jugular vein and vehicle control groups were identical to vincristine infusion model, except for administration of vehicles.

Tactile sensitivity (Mechanical allodynia) was evaluated using von Frey monofilaments before and after treatment, and animals were used withdrawal threshold value was less than 4 g. One week after surgery, vincristine-infused animals (n=6), sham-operated animals (n=12) and vehicle-operated (n=18) animals were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method. The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compound of Example 1 was evaluated at the dose of 1, 5 and 10 mg/kg (n=6), intraperitoneally administrated in a volume of 5 ul/g, bw in a vehicle of 30% (v/v) PEG. The test was performed at the peak time of efficacy (0.5 hr) after compound administration.

Figure 6:
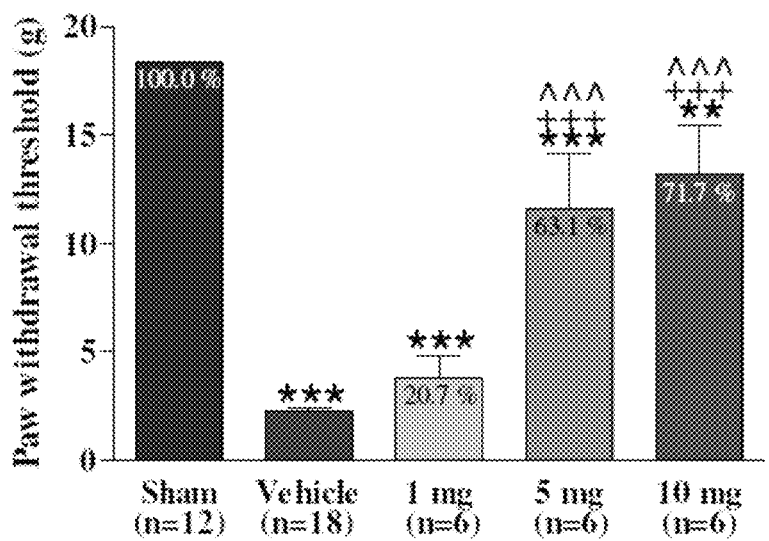
FIG. 6 is a graph showing paw withdrawal threshold measured by using the von Frey monofilament for Compound 1 (on vincristine-induced pain model), wherein the values (% control) are expressed as the mean±S.E.M. (n=6~18), and statistical analysis was used by One-way ANOVA at 0.5 hr: $F(4.43)=62.81$, $p<0.0001$ (Tukey's test)*; vs Sham, $p<0.001$, ; vs Sham, $p<0.01$, +++; vs Vehicle, $p<0.001$, ^^^; vs 1 mg, $p<0.001$.

The relative values compared to the sham (% control) were calculated and shown in Table 6 and FIG. 6, which show an antiallodynic effect of Compound 1 on vincristine-induced pain model in rats.

TABLE 6

Antiallodynic effect of Compound 1 on Vincristine-induced pain model

| Example No. | Name of Compounds | Vehicle | Dose (mg/kg) | % Control |
|---|---|---|---|---|
| 1 | 1-(2-chlorophenyl)-(S)-1-hydroxypropyl-(S)-2-carbamate (SS) | 30% PEG 400 | 1 | 20.7% |
| | | | 5 | 63.1% |
| | | | 10 | 71.7% |

Experimental Example 5

Evaluation of Antiallodynic Activity on Complete Freund's Adjuvant (CFA)-Induced Inflammatory Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

CFA-induced inflammatory pain was induced by the procedure of Nagakura et al. (2003) and Gregory P. et al. (2010) with minor modifications. CFA (sigma, USA) was injected in the right plantar with a 100 ul volume under gaseous anesthesia with isoflurane a 4:4 flow ratio of $NO_2$. Sham controls were injected with 100 ul of saline and vehicle controls were identical to CFA infusion model, except for administration of vehicles.

Tactile sensitivity (Mechanical allodynia) was evaluated using von Frey monofilaments before and after treatment, and animals were used withdrawal threshold value was less than 4 g. One week after surgery, CFA-infused animals (n=4~6), sham-operated animals (n=12), and vehicle-operated animals (n=17) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compound of Example 1 was evaluated at the dose of 10, 30 and 60 mg/kg (n=4~6), intraperitoneally administered in a volume of 5 ul/g bw in a vehicle of 30% (v/v) PEG. The test was performed peak time of efficacy (0.5 hr) after compound administration.

Figure 7:
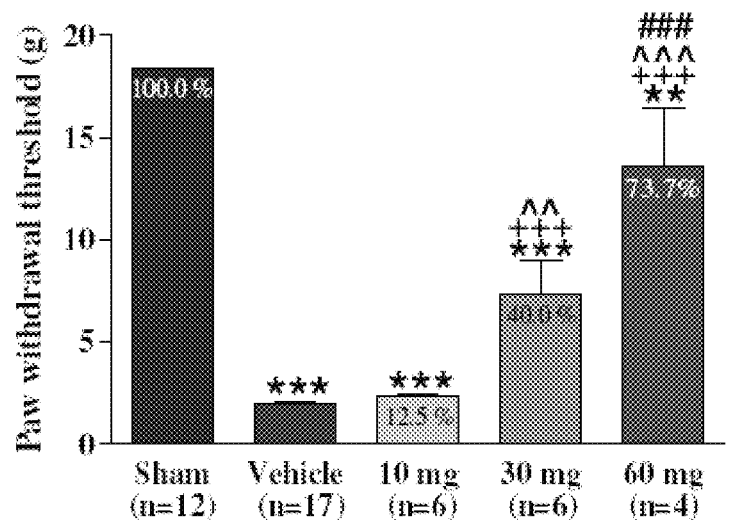
FIG. 7 is a graph showing paw withdrawal threshold measured by using the von Frey monofilament for Compound 1 (on CFA-induced pain model), wherein the values (% control) are expressed as the mean±S.E.M. (n=4~17), and statistical analysis was used by One-way ANOVA at 0.5 hr: $F(4.40)=123.6$, $p<0.0001$ (Tukey's test)*; vs Sham, $p<0.001$, ; vs Sham, $p<0.01$, +++; vs Vehicle, $p<0.001$, ^^^; vs 10 mg, $p<0.001$, ^^; vs 10 mg, $p<0.01$, ###; vs 30 mg, $p<0.001$.

The relative values compared to the sham (% control) were calculated and shown in Table 7 and FIG. 7, which show an antiallodynic effect of Compound 1 on CFA-induced pain model in rats.

TABLE 7

Antiallodynic effect of compound example 1 on CFA-induced pain model

| Example No. | Name of Compounds | Vehicle | Dose (mg/kg) | % Control |
|---|---|---|---|---|
| 1 | 1-(2-chlorophenyl)-(S)-1-hydroxypropyl-(S)-2-carbamate (SS) | 30% PEG 400 | 10 | 12.5% |
| | | | 30 | 40.0% |
| | | | 60 | 73.7% |

Experimental Example 6

Evaluation of Antiallodynic Activity on Streptozotocin (STZ)-Induced Diabetic Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

STZ-induced diabetic pain model was established with a modified method of Rakieten et al. (1963) and Bertrand Aubel et al. (2004). All animals were fasted 4 to 6 hr prior to STZ injection. STZ (sigma, USA) was dissolved in 20 mM sodium citrate buffer, pH 5.5 (sigma, USA) and intraperitoneally injected at 75 mg/kg, 4 ul/g, bw into the rats Sham controls were injected with same volume of 20 mM sodium citrate buffer, pH 5.5 and vehicle controls were identical to STZ model, except for administration of vehicles. Rats were supplied with 10% sucrose water for 2 days against sudden hypoglycemia. 3 days later, the induction of diabetes was checked by measurement of tail vein blood glucose levels with a blood glucose meter. (LifeScan OneTouch Ultra, USA). If blood glucose was not >300 mg/dl by 72 hr, the rat was excluded from the diabetic group.

Tactile sensitivity (Mechanical allodynia) was evaluated using von Frey monofilaments before and after treatment of compound example 1 and animals were used withdrawal threshold value was less than 4 g. One week after surgery, diabetic animals (n=6), sham controls (n=12), and vehicle control (n=18) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

Antiallodynic effect of compound of Example 1 was evaluated at the dose of 10, 30 and 60 mg/kg (n=6), intraperitoneally administrated in a volume of 5 ul/g, bw in a vehicle of 30% (v/v) PEG. The test was performed at the peak time of efficacy (0.5 hr) after compound administration.

Figure 8:
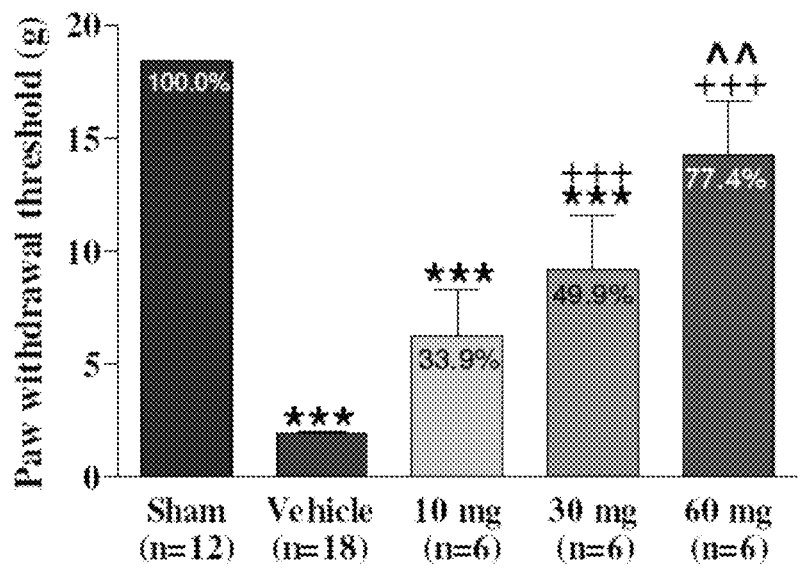
FIG. 8 is a graph showing paw withdrawal threshold measured by using the von Frey monofilament for Compound 1 (on STZ-induced pain model), wherein the values (% control) are expressed as the mean±S.E.M. (n=6~18), and statistical analysis was used by One-way ANOVA at 0.5 hr: $F(4.43)=48.33$, $p<0.0001$ (Tukey's test)***; vs Sham, $p<0.001$, +++; vs Vehicle, $p<0.001$, ^^; vs 10 mg, $p<0.01$.

The relative values compared to the sham (% control) were calculated and shown in Table 8 and FIG. 8, which show an antiallodynic effect of Compound 1 on STZ-induced pain model in rats.

TABLE 8

Antiallodynic effect of compound example 1 on STZ-induced pain model

| Example No. | Name of Compounds | Vehicle | Dose (mg/kg) | % Control |
|---|---|---|---|---|
| 1 | 1-(2-chlorophenyl)-(S)-1-hydroxypropyl-(S)-2-carbamate (SS) | 30% PEG 400 | 10 | 33.9% |
|  |  |  | 30 | 49.9% |
|  |  |  | 60 | 73.7% |

Experimental Example 7

Measurement of Neurotoxicity

The measurement of neurotoxicity of the test compounds was conducted by the method of Dunham and Miya [Dunham, N. W. and Miya, T. S. 1957. A note on a simple apparatus for detecting neurological deficit in rats and mice. J. Am. Pharm. Assoc. (Baltimore) 46: 208-209]. In the method, motor abilities of the test animals can be determined by observing whether the test animals can walk without falling from a rotator, thereby determining the value of neurotoxicity of each compound. Term "TD50" means the respective dose of the test compound at which 50% of the test animal exhibit neurotoxicity. They were pre-trained on the rotarod (Rotarod; Columbus instrument, rota-max, USA) at 6 rpm for 5 min 24 hr prior to the test. The peak time was determined by administration test material's random dose for 0.5, 1, 2, 4 hour. To evaluate the minimal neurotoxicity of the compound, the mice were placed on the Rotarod (rod circle; 3 Cm) at 6 rpm and the test animal fails to maintain walking once or more during 1 minute, it can be regarded that the test animal exhibits neurotoxicity. The ratio of TD50 to ED50 (TD50/ED50) is called as a protective index, and useful as a parameter for comparison of pharmaceutical efficacy and neurotoxicity. The obtained results are shown in following Table 10.

TABLE 10

Measurement results of neurotoxicity of compounds in the test animals

| No. | TD50 (mg/kg po) | PI(TD50/ED50 in MES) |
|---|---|---|
| 1 | 218.1 | 16.8 |
| 2 | 372.0 | 7.3 |
| 3 | 378.3 | 12.0 |
| 5 | 275.2 | 3.3 |
| 37 | 131.6 | 5.1 |

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

What is claimed is:

1. A method of alleviating or treating pain comprising administering a pharmaceutically effective amount of a compound represented by Chemical Formula 1 or a pharmaceutically acceptable salt thereof, to a subject in need of alleviating or treating pain which is not a muscle spasm-associated pain:

[Chemical formula 1]

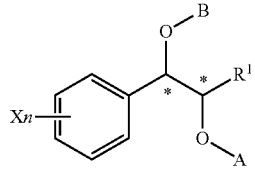

wherein
X is a halogen;
n is an integer from 1 to 5;
$R^1$ is a linear or branched alkyl group of $C_1$-$C_4$;
A is a carbamoyl derivative represented by

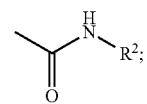

B is hydrogen;
and
$R^2$ is selected from the group consisting of hydrogen, a linear or branched alkyl group of $C_1$-$C_4$, a cycloalkyl group of $C_3$-$C_8$, and benzyl group,
wherein the compound represented by the Chemical Formula 1 is the sole active agent that alleviates or treats the pain which is not a muscle spasm-associated pain.

2. The method according to claim 1, wherein
X is chlorine, fluorine, iodine, or bromine;
n is 1 or 2;
$R^1$ is methyl group, ethyl group, isopropyl group, or butyl group;
A is a carbamoyl derivative represented by

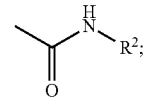

B is hydrogen,
and
$R^2$ is selected from the group consisting of hydrogen, methyl group, propyl group, isopropyl group, cyclopropyl group, cyclohexyl group, bicycloheptane group, and benzyl group.

3. The method according to claim 1, wherein the compound is selected from the group consisting of:
1-(2-chlorophenyl)-1-hydroxypropyl-2-carbamate,
1-(2-chlorophenyl)-1-hydroxybutyl-2-carbamate, 1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate,
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate, and
1-(2,3-dichlorophenyl)-1-hydroxypropyl-2-carbamate.

4. The method according to claim 1, wherein the compound is in the form of racemate, enantiomer, diastereomer, a mixture of enantiomer, or a mixture of diastereomer.

5. The method according to claim 1, wherein the pain is one or more selected from the group consisting of nociceptive pain, psychogenic pain, inflammatory pain, and pathological pain.

6. The method according to claim 1, wherein the pain is one or more selected from the group consisting of neuropathic pain, cancer pain, postoperative pain, trigeminal neuralgia pain, idiopathic pain, diabetic neuropathic pain, and migraine.

7. The method according to claim 1, wherein the compound is selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
Racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxybutyl-(S)-2-carbamate,
Racemate of 1-(2-chlorophenyl)-(S)-1-hydroxybutyl-(S)-2-carbamate and 1-(2-chlorophenyl)-(R)-1-hydroxybutyl-(R)-2-carbamate,
1-(2-chlorophenyl)-(S)-1-hydroxy-3-methyl-butyl-(S)-2-carbamate,
Racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(S)-2-N-isopropylcarbamate,
1-(2-chlorophenyl)-(S)-1-hydroxypropyl-(S)-2-N-cyclopropylcarbamate,
1-(2-chlorophenyl)-(S)-1-hydroxypropyl-(S)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
Racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate,
Racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
Racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
Racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
Racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, and
1-(2-iodophenyl)-(S)-1-hydroxybutyl-(S)-2-carbamate.

8. The method according to claim 5, wherein the compound is selected from the group consisting of:
1-(2-chlorophenyl)-1-hydroxypropyl-2-carbamate,
1-(2-chlorophenyl)-1-hydroxybutyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate, 1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate, and
1-(2,3-dichlorophenyl)-1-hydroxypropyl-2-carbamate.

* * * * *